(12) United States Patent
Kelly et al.

(10) Patent No.: US 8,678,252 B2
(45) Date of Patent: Mar. 25, 2014

(54) APPARATUS AND METHOD FOR DONNING A GLOVE

(75) Inventors: Patrick Kelly, Nottingham (GB); Simon M. Webb, Leamington Spa (GB)

(73) Assignee: My Safe Hands Limited, Coventry (GB)

( * ) Notice: Subject to any disclaimer, the term of this patent is extended or adjusted under 35 U.S.C. 154(b) by 748 days.

(21) Appl. No.: 12/600,443

(22) PCT Filed: May 14, 2008

(86) PCT No.: PCT/GB2008/001662
§ 371 (c)(1),
(2), (4) Date: Feb. 12, 2010

(87) PCT Pub. No.: WO2008/139192
PCT Pub. Date: Nov. 20, 2008

(65) Prior Publication Data
US 2010/0147909 A1    Jun. 17, 2010

(30) Foreign Application Priority Data

May 14, 2007  (GB) .................................. 0709239.8
Dec. 10, 2007  (GB) .................................. 0724095.5

(51) Int. Cl.
*A47G 25/80*    (2006.01)
(52) U.S. Cl.
USPC ........................................................... 223/111
(58) Field of Classification Search
USPC ................ 223/111, 112; 2/16, 158, 159, 160, 2/161.7, 901, 161.6, 162, 910, 917; 128/856, 878, 879; 604/292; 602/21
See application file for complete search history.

(56) References Cited

U.S. PATENT DOCUMENTS 3,283,338 A * 11/1966 Landau .......................... 2/161.6
4,002,276 A *  1/1977 Poncy et al. .................... 223/111

(Continued)

FOREIGN PATENT DOCUMENTS

| GB | 2001520 A | 2/1979 |
|---|---|---|
| JP | 10000202 A | 1/1998 |
| JP | 10108870 A | 4/1998 |
| WO | 2005/053477 A1 | 6/2005 |

OTHER PUBLICATIONS

Burgos, International Search Report and Written Opinion of ISA, PCT/GB08/01662, Aug. 8, 2008.

*Primary Examiner* — Clinton T Ostrup
*Assistant Examiner* — Andrew Sutton
(74) *Attorney, Agent, or Firm* — Michael A. Mann; Nexsen Pruet, LLC

(57) ABSTRACT

The present invention provides a support (200) for a glove (300). The support (200) is configured to releasably retain a glove (300) in a position which enables the glove (300) to be donned by a user and comprises a planar body (202) having at least one digit aperture (204,206,208,210,212) shaped to receive the fingers of a user, an inner glove retaining arrangement (230) provided around the at least one digit aperture (204,206,208,210,212), and an outer glove retaining arrangement (242) provided around both the first glove retaining arrangement (230) and the at least one digit aperture (204, 206,208,210,212). The body (202) further includes at least one weakened region (220,222) extending from the at least one digit aperture (204,206,208,210,212), the weakened region (220,222), in use, permitting the body (202) to tear and thereby increase the size of the at least one digit aperture (204,206,208,210,212) as the hand of a user is inserted into the at least one digit aperture (204,206,208,210,212).

23 Claims, 19 Drawing Sheets

(56) References Cited

U.S. PATENT DOCUMENTS

| | | | | |
|---|---|---|---|---|
| 4,069,913 A | | 1/1978 | Harrigan | 206/278 |
| 4,155,494 A | * | 5/1979 | Poncy et al. | 223/111 |
| 4,275,812 A | * | 6/1981 | Poncy et al. | 206/278 |
| 4,677,697 A | * | 7/1987 | Hayes | 2/159 |
| 4,889,266 A | * | 12/1989 | Wight | 223/111 |
| 4,898,309 A | | 2/1990 | Fischer | 223/111 |
| 4,971,233 A | * | 11/1990 | Keenan | 223/111 |
| 5,769,289 A | | 6/1998 | Lusk | 223/112 |
| 5,816,440 A | * | 10/1998 | Shields et al. | 221/45 |
| 6,168,019 B1 | * | 1/2001 | Olson | 206/390 |
| 6,419,131 B1 | | 7/2002 | Rix | 223/111 |
| 6,485,467 B1 | * | 11/2002 | Crook et al. | 604/174 |
| 6,748,605 B1 | * | 6/2004 | Brinkmann | 2/161.6 |
| 6,871,359 B2 | * | 3/2005 | Han | 2/161.6 |
| 7,377,410 B1 | * | 5/2008 | Webb | 223/111 |
| 7,624,456 B2 | * | 12/2009 | Williams et al. | 2/169 |
| 7,805,772 B2 | * | 10/2010 | Williams | 2/111 |
| 2006/0010563 A1 | | 1/2006 | Michel et al. | 223/111 |
| 2006/0144878 A1 | * | 7/2006 | Williams | 223/111 |
| 2007/0170213 A1 | * | 7/2007 | Gaines et al. | 223/111 |
| 2008/0073388 A1 | * | 3/2008 | Saegusa | 223/111 |
| 2008/0110944 A1 | * | 5/2008 | Webb | 223/111 |
| 2009/0188018 A1 | * | 7/2009 | Bates et al. | 2/158 |
| 2009/0307825 A1 | * | 12/2009 | Bhalla | 2/161.7 |
| 2010/0147909 A1 | * | 6/2010 | Kelly et al. | 223/111 |

* cited by examiner

Front view    Side view

Front view	Side view

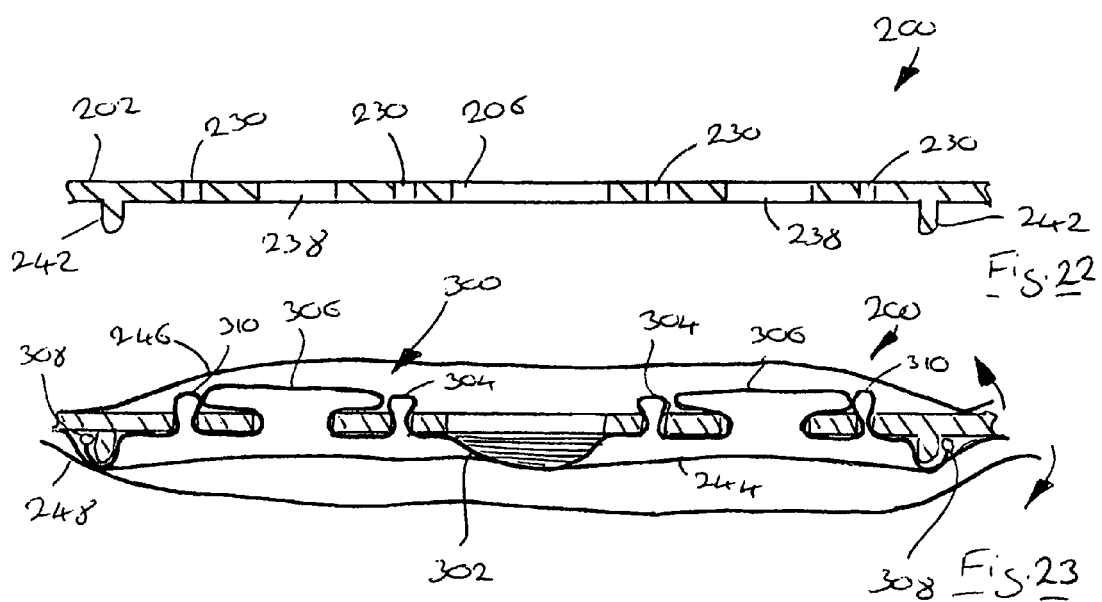

APPARATUS AND METHOD FOR DONNING A GLOVE

RELATED APPLICATIONS

This application is a National Phase Application of PCT Patent Application No. PCT/GB2008/001662 having an International Filing Date of May 14, 2008, which itself claims the benefit under PCT Rule 4.10 of GB0709239.8, filed May 14, 2007, and GB0724095.5, filed Dec. 10, 2007.

The contents of the related applications, above, are incorporated by reference as if fully set forth herein.

FIELD AND BACKGROUND OF THE INVENTION

This invention relates to a glove, a device for holding a glove, an apparatus for donning a glove comprising the combination of the glove holding device and a glove and a method of donning a glove using the apparatus. The invention is particularly concerned, though not exclusively, with the use of the apparatus with a sterile glove to allow the glove to be put on easily whilst maintaining the sterility of the glove. The invention is equally applicable to the donning of non-sterile gloves.

Gloves, including surgical gloves, are worn in a variety of environments that demand sterility, for example, in medical, laboratory, food-preparation and manufacturing "clean room" environments. There are numerous situations in which it is important to maintain the sterility of a glove as it is being donned.

In the medical environment, gloves are worn to prevent the hands of medical professionals from contacting a patient's body during a physical examination or a surgical operation. Protective gloves, in general, are universally recognised as a major safeguard against the risk of inadvertent or accidental infection or cross contamination of patients, of the wearer of the gloves and of the medical environment.

For example, the use of a single sterile glove on the non-dominant hand may be used to feel over a vein during the performance of a venipuncture to prevent contamination of a patient's bloodstream.

In the manufacturing "clean room" environment, gloves are worn to prevent the hands of a technician from directly contacting items, such as wafers and other devices supporting highly sensitive electronic circuits. Wearing non-sterile gloves in such an environment may lead to contamination of such items, making them unsuitable for use.

It is of the utmost importance that gloves that are manufactured to be sterile are kept in a sterile condition during storage. Where gloves are initially sterile it is often highly desirable, and in some cases mandatory, that the sterility of the gloves be maintained during the donning process. Sterility of the glove can be adversely affected during the process in which the wearer puts on or dons the gloves. Accordingly, the putting on or donning process is a major point of contamination of the sterile gloves. During the donning process, the hands or other sources of contamination can contact and contaminate the sterile gloves by the inadvertent transfer of microbes or other contaminants to the sterile glove surfaces.

In the medical profession, the risk of undesirable contamination arising during the donning process is reduced by putting the glove on by using one of two generally accepted techniques for unassisted donning. These two techniques are open glove donning and closed glove donning.

The open glove donning technique now used for donning gloves, for example surgical gloves, requires that the sealed package containing the sterile gloves be carefully opened so that the inner surfaces of the package, and more particularly, the outside surfaces of the gloves contained therein, do not come in contact with any non-sterile surface. The gloves are usually packaged with their cuffs averted; that is, turned inside out and folded downwardly. To don the right glove, the wearer grasps the right glove on the fold of the averted cuff with the left hand and the right hand is inserted into the glove opening. Next, the left glove is picked up and held with the right hand by slipping the gloved fingers of that hand underneath the averted cuff while the left hand is inserted into the glove opening. To complete glove donning, the averted cuffs are carefully pulled over the distal ends of the garment's sleeves so that the entirety of the previously exposed surfaces of the averted cuffs are on the insides of the gloves and the outsides remain untouched by un-gloved hands.

In the closed glove donning technique, the gloves are handled through the fabric of the sleeve itself, for example a surgical gown sleeve. As such, the wearer's hand does not extend outside from the sleeve until the open end of the glove is actually pulled over the sleeve. The closed glove donning technique may best be conveyed by describing its current use in a surgical arena. This method assumes that the wearer is already wearing a sterile surgical gown. Accordingly, the wearer uses the left hand while keeping it within the sleeve of the gown to pick up the right glove by its averted cuff. In this manner, the glove itself is not directly touched since the left hand is shielded by the sleeve. With the right hand extended palm upward but retained within the sleeve, the left hand places the palm of the glove with fingers pointing towards the wearer against the retained palm of the right hand. The closest edge of the averted cuff is grasped by the right hand through the sleeve fabric. Next, the left hand pulls the un-grasped averted cuff edge over the right sleeve and hand. The left hand is gloved in the same manner using the gloved right hand to appropriately place the left glove and pull it over the left sleeve and hand.

Both glove donning methods entail difficulties. The open glove donning technique requires a high level of finger and hand dexterity. The closed glove donning technique suffers from finger and hand dexterity being hampered while one's fingers remain shielded by the sleeve. As would be expected by such complex procedures, they are susceptible to numerous accidental contamination possibilities, especially during times of distress and urgency. Thus, a better method is needed that enables the wearer to don gloves without using the open or closed methods but using a method which is quicker, easier, more controlled, simple to practice, preformed, sterile and which does not necessitate the help of an assistant. In addition, this method should be economically cost effective to implement and practice.

In dental care settings, where the dentist or dental assistant is obliged to work inside the mouth, post-treatment infections occur because of poor hygiene practice. For example, dental office surveys by means of hidden video cameras revealed that sampled dentists wash their hands before donning gloves in only 23% of patient contacts and changed gloves between patients in only 56% of contacts (Porter et al. British Medical Journal 1996; 312: 705). By providing an improved method of donning sterile gloves which is quicker, easier and more efficient than existing methods, dentists and dental assistants are more likely to change gloves between patient contacts and the likelihood of the gloves becoming contaminated during the donning process is reduced. This would have the effect of reducing post-treatment infections.

The magnitude of the un-sterile glove problem comes into focus when one considers:

1. Apart from designated surgical operating rooms, un-sterile examination gloves are currently estimated at being used at the rate of more than 10 billion/yr. in U.S. health care facilities.
2. Studies by trained observers in sampled intensive care units and emergency rooms reveal that health care workers wash their hands before and after each patient contact only 20-40% of the time (Wurtz et al. Am. J. Infect. Control 1994; 22: 228-230; Nystrom. Infect. Control Hosp. Epidemiol. 1994; 15: 435-436; Meengs et al. J. Emerg. Nurs. 1994; 20: 183-188).
3. A survey found that health care workers washed their hands before putting on examinations gloves, only 27 times out of a hundred (Thompson B. L. et al. Infect. Control Hosp. Epidemiol. 1997; 18: 97-103).
4. The increased use of latex gloves by health care workers to protect themselves from HIV and HBV infections has led to a false sense of security among health care workers and patients and has lead to wide-spread failure to wash bands properly and adequately during patient care (Heptonstall & Mortimer. Lancet 1995; 345: 599-600).

The above examples demonstrate that there is high prevalence of failure to wash hands properly, if at all, between patient contacts amongst health care workers and dentists. Therefore, in these situations, the risk of contamination of a sterile glove coming into contact with an unwashed hand is far higher than if the hand had been thoroughly washed. An improved method of donning a sterile glove which minimises the risk of an unwashed hand coming into contact with the sterile outer surface of the glove would significantly reduce the chances of contamination. This, in turn, would reduce the chances of post operative infection, cross contamination, etc.

In the manufacturing "clean room" environment, an improved method of donning a sterile glove would also significantly reduce the chances of contamination. In this situation, contamination might be from grease, oil or other residues on the wearers hands which could severely affect any electronic circuits or other highly sensitive electronic equipment if such contaminants were to come into contact with the electronic circuits or equipment.

As can be seen, it is highly desirable to develop an apparatus and/or method which allows the donning of sterile gloves to be quicker, easier, more controlled, simpler to practice, preformed, sterile and which does not necessitate the help of an assistant. In addition, this apparatus and/or method should be economically cost effective to implement and practice.

SUMMARY OF THE INVENTION

An object of the present invention is to minimise the risk of contamination of a sterile glove during the donning process.

A further object of the invention is to increase the speed and ease by which a glove or pair of gloves can be donned.

Another object of the invention is to reduce the temptation amongst workers in sterile environments not to use gloves or not to change their gloves by using the present invention rather than current cumbersome methods.

According to the present invention there is provided a support for a glove, the support being configured so as to releasably retain a glove in a position which enables the glove to be donned by a user, the support comprising a planar body having at least one digit aperture shaped to receive the fingers of a user, an inner glove retaining arrangement provided around the at least one aperture, and an outer glove retaining arrangement provided around both the first glove retaining arrangement and the at least one aperture, wherein the body includes at least one weakened region extending from the at least one digit aperture, the weakened region, in use, permitting the body to separate and thereby increase the size of the aperture as the hand of a user is inserted into the at least one digit aperture.

The weakened region of the body may tear, break or otherwise separate to permanently increase the size of the at least one digit aperture.

An object of the support is to hold the open end of a glove in an open position so that it is relatively quick and easy for a user to insert a hand into the open end of the glove, thereby donning the glove. Further, by maintaining the open end of the glove in an open position, the finger and thumb portions of the glove are clearly exposed allowing the fingers and thumb of a hand to be more quickly and easily inserted into the finger and thumb portions. This makes the glove donning process extremely straightforward which reduces the risk of contaminating the glove during the donning process. The support permits a user to don a glove in a single handed manner. The support fulfils the function of holding the glove which would otherwise be undertaken by the free hand of the user.

A further object of the invention is to allow a hand to be inserted into the glove without coming into contact with the external surface of the glove. This ensures that no contamination is transferred from the hand to the external surface of the glove when the glove is donned.

The tearing or breaking of the at least one weakened region of the support permanently increases the size of the at least one aperture.

The planar body may preferably comprise a flexible sheet of material. The planar body may preferably comprise a flexible sheet of plastics material.

The at least one digit aperture of the body is sized such that the fingers of a user are able to enter and pass through the aperture, however the palm of the hand of a user is not. The body is provided with one or more weakened regions which extend across the body from the aperture and which enable the body to tear or break in a predetermined manner to increase the size of the aperture and thereby allow the hand of the user to pass through the aperture.

The at least one weakened region may be defined by a line of perforations in the body. Alternatively, the at least one weakened region may be defined by a score or similar indentation of the body. In yet a further embodiment, the at least one weakened region may be defined by a portion of the body which has been treated so as to be weaker than the remainder of the body, for example, the weakened region may have been treated so as to be more brittle than the remainder of the body. In yet a further embodiment, the at least one weakened region may be defined by a cut or break in the body which has been temporarily repaired.

The body may be provided with a plurality of apertures shaped to receive the fingers of a user. The body may for example be provided with five separate apertures shaped to receive the thumb, index, middle, ring and little fingers of a user. Alternatively, the body may be provided with a first aperture shaped to receive a thumb of a user and a second aperture shaped to receive the index, middle, ring and little fingers of a user. It will be appreciated the other aperture configurations are possible. Where multiple apertures are provided it will be appreciated that a portion of the body in the form of a web is provided between the apertures. The web is configured so as to break, in use, and thus not to hinder the passage of the hand of a user through the support. As with the weakened region, the or each web may be provided with, a line of perforations or a score or similar indentation of the body. Alternatively, the web may be treated so as to be weaker than the remainder of the body, for example, the web may have been treated so as to be more brittle than the remainder of the body.

The inner glove retaining arrangement, in use, retains a glove in a position where the fingers of the glove are aligned with the at least one aperture of the body. The inner glove retaining arrangement thus engages the glove at portions of the palm and back glove which surround the base of the fingers of the glove. The inner glove retaining arrangement may comprise a plurality of formations of the body which surround the at least one aperture. The formations may comprise apertures or holes extending through the body into which portions of a glove may be placed. In such an embodiment, each aperture may comprise a slot. In an alternative embodiment, the formations may comprise recesses of the body into which portions of a glove may be placed. In yet a further embodiment, the inner glove retaining arrangement may comprise an adhesive applied to body which, in use, temporarily adheres a glove to the body.

The outer glove retaining arrangement, in use, retains the cuff of a glove to the body. Preferably, the outer glove retaining arrangement retains the cuff bead of a glove. The outer glove retaining arrangement may comprise one or more formations of the body. In such an embodiment, the outer glove retaining arrangement may comprise a projection of the body. The projection may take the form of a lip. The lip may be continuous or discontinuous. The formations may comprise apertures or holes extending through the body into which portions of a glove may be placed. In such an embodiment, each aperture may comprise a slot. In an alternative embodiment, the formations may comprise recesses of the body into which portions of a glove may be placed. In yet a further embodiment, the outer glove retaining arrangement may comprise an adhesive applied to body which, in use, temporarily adheres a desired portion of a glove to the body.

The support may be provided with a glove storage arrangement which is provided between the inner and outer glove retention arrangements. The glove storage arrangement may comprise one or more apertures of the body through which portions of a glove may pass, in use. The or each glove storage aperture is intended to receive a portion of a glove which extends between the cuff of a glove and the area at which the fingers of a glove meet the palm and back of a glove. Portions of the glove received in the or each storage aperture may be rolled, folded, placed in a concertina formation or otherwise stored. In an alternative embodiment, the glove storage arrangement may comprise one or more recesses of the support into which the aforementioned portions of a glove may be received. In yet a further arrangement, the glove storage arrangement may comprise at least one region of adhesive provided on the body by which the aforementioned portions of a glove may be temporarily retained.

Optionally the support may be provided with an additional glove retaining arrangement which is positioned between the glove storage arrangement and the outer glove retaining arrangement. The additional glove retaining arrangement may comprise a plurality of formations of the body which surround the glove storage arrangement of the support. The formations may comprise apertures or holes extending through the body into which portions of a glove may be placed. In such an embodiment, each aperture may comprise a slot. In an alternative embodiment, the formations may comprise recesses of the body into which portions of a glove may be placed. In yet a further embodiment, the additional glove retaining arrangement may comprise an adhesive applied to body which, in use, temporarily adheres desired portions of the glove to the body.

The support may be configured so as to releasably retain a pair of gloves comprising a left hand glove and a right hand glove. In such an embodiment the support may comprise a body having at least one left digit aperture and at least one right digit aperture shaped to receive the fingers of the respective left and right hands of a user, an inner glove retaining arrangement provided around each of the at least one digit apertures, and respective outer glove retaining arrangements provided around each first glove retaining arrangement and each of the at least one digit apertures, wherein the body includes at least one weakened region extending from each of the at least one digit apertures, the weakened regions, in use, permitting the body to tear and thereby increase the size of the respective digit apertures as the hands of a user is inserted into each of the at least one digit apertures.

The support may be configured so as to releasably retain a plurality of gloves or a plurality of pairs of gloves. In such an embodiment the support is provided with repeated arrays of the features described above which enable multiple gloves or multiple pairs of gloves to be releasably retained thereby.

According to a further aspect of the present invention, there is provided the combination of a support and a glove, the support being configured so as to releasably retain the glove in a position which enables the glove to be donned by a user, the support comprising a planar body having at least one digit aperture shaped to receive the fingers of a user, an inner glove retaining arrangement provided around the at least one aperture, and an outer glove retaining arrangement provided around both the first glove retaining arrangement and the at least one aperture, wherein the body includes at least one weakened region extending from the at least one digit aperture, the weakened region, in use, permitting the body to tear and thereby increase the size of the aperture as the hand of a user is inserted into the at least one digit aperture, wherein the cuff of the glove is releasably retained by the outer glove retaining arrangement and portions of the palm and back of the glove which surround the base of the fingers of the glove are retained in the inner glove retaining arrangement such that the fingers of the glove are aligned with the at least one digit aperture. Features of the support described above are equally applicable to the support when combined with a glove.

The support co-operates with the glove to retain the openings to the fingers of the glove at a position substantially at or within the plane of the support.

The glove is provided on a side of the support which faces away from the user, in use. The user is thus able to view the interior of the glove through the at least one digit aperture.

The support may be provided with a protective cover which forms a sealed compartment with the support, and wherein the external surface of the glove is positioned on the interior of the sealed compartment. The cover, and, hence the sealed compartment, is provided on a side of the support which faces away from the user, in use. The cover may be made of any suitable material. The cover may be a thin membrane, film or other light, flexible material. The sealed compartment can be manufactured as an air tight package or vacuum sealed. Preferably, the cover is formed such that it can become detached from the support when the glove is donned. This may occur as a result of force applied thereto by the movement of a users fingers against the cover as the user dons the glove causing the cover to become detached from the support. Alternatively, the cover may be removed from the support immediately prior to the glove being donned. The cover may be manually removable by the user or may be removed automatically by an apparatus containing the support.

Instead of the cover becoming detached from the support, the cover itself may split or tear allowing the glove and hand to pass therethrough. This may be achieved by having perforations or lines of weakened material in the cover, or the material cover may be sufficiently thin that force applied thereto by the hand of a user causes the cover to break.

Preferably, the sealed compartment is sterile so that the external surface of the glove remains sterile while the glove is retained within the sealed compartment. The sealed compartment may further contain a chemical or active ingredient to ensure the compartment is kept sterile, for example, a disinfectant or anti-bacterial agent.

The cover preferably fits closely to the support and thus holds the fingers of the glove close to the support in the region of the at least one digit aperture. The fingers of the glove may be folded, rolled, placed in a concertina fashion or otherwise stored so as to enable them to be held close to the support by the cover.

The support may be provided with an additional cover which is provided on the side of the support which faces the user, in use. The additional cover overlies the at least one digit aperture and requires removal from the support before a user dons the glove. Where the support is provided with additional apertures forming an inner glove retaining arrangement, a glove storage arrangement and/or an additional glove retaining arrangement, the additional cover may overlie these apertures and portions of the glove extending therethrough to the side of the support facing the user. The additional cover may comprise a flexible sheet or film. The additional cover may comprise a sheet of plastic material.

The support may optionally be provided with a further cover which overlies the protective cover and which is removable prior to the user donning the glove. This further cover may be provided so as maintain the outer surface of the protective cover in a sterile state. The further cover may comprise a flexible sheet or film. The further cover may comprise a sheet of plastic material.

The invention also provides a method of donning a glove onto a hand of a user using a glove support, the method comprising the steps of:
  providing a support comprising a planar body having at least one digit aperture shaped to receive the fingers of a user, an inner glove retaining arrangement provided around the at least one aperture, and an outer glove retaining arrangement provided around both the first glove retaining arrangement and the at least one aperture, wherein the body includes at least one weakened region extending from the at least one digit aperture,
  providing a glove mounted to the support such that the cuff of the glove is releasably retained by the outer glove retaining arrangement and portions of the palm and back of the glove which surround the base of the fingers and thumb of the glove are retained in the inner glove retaining arrangement such that the finger and thumb of the glove are aligned with the at least one digit aperture
  aligning the fingers and thumb of the hand of the user with the finger and thumb portions of the glove;
  inserting the fingers and thumb of the hand into the finger and thumb portions of the glove through the at least one digit aperture;
  moving the hand of the user through the at least one digit aperture to cause the weakened region of the support to break and thereby enlarge the at least one digit aperture and the glove to become disengaged from the inner and then the outer glove retaining arrangements and become donned to the hand of the user; and
  retrieving the gloved hand by moving it back through the enlarged aperture.

According to a further aspect of the present invention there is provided a glove donning apparatus comprising a member defining an aperture, the member having means for detachably retaining a glove disposed around the perimeter of the aperture and a glove retained by the retaining means, the retaining means comprising an inner glove retaining formation extending around the aperture and an outer glove retaining formation extending around both the inner glove retaining formation and the aperture, wherein the retaining means hold the glove in tension across the aperture such that the finger and thumb apertures of the glove are positioned across the aperture.

An object of the glove donning apparatus is to hold the open end of a glove in an open position so that it is relatively quick and easy to insert a hand into the open end of the glove, thereby donning the glove. Further, by maintaining the open end of the glove in an open position, the finger and thumb portions of the glove are more clearly exposed allowing the fingers and thumb of a hand to be more quickly and easily inserted into the finger and thumb portions. This makes the glove donning process extremely straightforward which reduces the risk of contaminating the glove during the donning process. The plate and the detachable retaining means of the plate are configured so as to enable the glove to be stretched at a predetermined tension across the aperture.

A further object of the invention is to allow a hand to be inserted into the glove without coming into contact with the external surface of the glove. This ensures that no contamination is transferred from the hand to the external surface of the glove when the glove is donned.

The plate may be any shape or size and may be flexible or rigid. The plate can be made from metal, cardboard, plastic, elastomer, rubber, a composite material or any other suitable material.

The aperture defined by the plate may be any shape or size. It may be circular, oval, elliptical, square, rectangular or any other suitable shape. Preferably, the aperture is oval. When the plate is formed from one piece of material, the aperture is preferably sized to allow a hand to pass therethrough.

The inner formation for detachably retaining a glove can be any suitable means so that the glove can be retained by said means and remain attached to the plate until such a time that sufficient force is applied to the glove to cause it to become detached from said formation. The inner retaining formation is disposed around the perimeter of the aperture so that the open end of a glove, when mounted on said formation, is held open and surrounds the aperture defined by the plate in such a way that an object passing through the aperture would pass through the open end of the glove into the interior of the glove. Preferably, the formation for detachably retaining the glove comprises a lip. The cross section of the lip may be circular, oval, elliptical, square, rectangular or any suitable shape which acts as a clip or holding mechanism to retain the glove prior to donning. Preferably, the lip comprises a continuous ring, having a circular cross-section, disposed around the perimeter of the aperture. The formation for detachably retaining the glove may be made from rigid or flexible plastic, metal, elastomer, rubber, cardboard, a composite material or any other suitable material. It may be made from the same or a different material from the plate.

The term "glove" is intended to cover conventionally configured gloves which cover the entire hand and have individual openings or sheaths for the fingers and thumb of the wearer. The term is also intended to cover mitten type gloves which cover the entire hand and have an opening for the fingers of the wearer and a separate opening for the thumb of the wearer. The term "glove" is also intended to encompass hand garments which only partially cover the hand of the wearer. Gloves of this type may, for example, comprise individual finger and thumb sheaths, or a glove which covers the fingers and thumb of a wearer but does extend fully across the palm of the wearer to their wrist.

For conventional gloves and mittens the term "cuff" is defined as the part of a glove defined by the open end of the glove on one side and extending along the glove from the open end to the palm area of the glove on the other side, just above the point at which the thumb portion of the glove connects to the palm area. When a glove is located on a users hand, the "cuff" will normally be surrounding the wrist and possibly the forearm of the user, depending on the length of the glove. Therefore, the "cuff" may be a large portion of the glove if it extends a significant way up the users arm. For the glove types mentioned above which only partially cover the hand of the wearer, the cuff may surround the base of one or more of the fingers or thumb of the wearer, or extend across the palm of the wearer.

The glove may be any suitable glove. Preferably the glove is an elasticised glove, for example, like the type commonly used by doctors, nurses and lab workers to protect the hands whilst not impairing dexterity. The glove can be a wet or dry type. The glove that is used may be a glove that is already on the market and widely available. Alternatively, it may be a purpose built bespoke glove, or a commercially available glove which has been adapted or modified accordingly. Generally, thin elasticised gloves that are widely available have beads at the open end of the glove. The term "bead" means the hardened, tightly rolled edge which forms the end of the glove at the open end. This bead may be used as a point of attachment so that the cuff retaining means retains the glove by cooperating with the cuff bead. When the cuff retaining means comprises a lip, said lip retains the bead attached to the cuff of the glove.

Preferably, the outer formation for detachably retaining the glove comprises a lip. The cross section of the lip may be circular, oval, elliptical, square, rectangular or any suitable shape which acts as a clip or holding mechanism to retain the cuff of the glove prior to donning. Preferably, the outer retaining formation comprises a continuous ring, having a circular cross-section, disposed around the inner retaining formation, being at a distance from the inner retaining formation.

The invention may further provides a glove comprising two beads positioned on the cuff of the glove positioned at a distance from each other. Preferably, the glove is an elasticised glove, for example, like the type commonly used by doctors, nurses and lab workers to protect the hands whilst not impairing dexterity. The glove may be made from natural or synthetic rubber, nitrite, latex, silicone, polyisoprene, composite, fibre, resin, plastic, elastomer, paper or any other suitable material such as natural materials, ecologically friendly and/or any chemical combination of materials. The glove may be any size. It is envisaged that different size gloves will be used for different embodiments of the invention to take into account the different size of the hands of potential users. The glove may be a range of different colours. Preferably, different sized gloves are colour-coded to indicate the size of the glove, and/or the nature of any active cleaning or sterile chemical agent applied to or incorporated, into the glove.

The glove according to the present invention may be manufactured with two beads positioned at a distance from each other. The glove can be any suitable type of glove. Alternatively, a commercially available glove may be used which already comprises one bead positioned on the cuff. Such gloves are well known to those skilled in the art. A second bead can be attached to the commercially available glove by a sticking or fixing process. Preferably, this is done during the manufacturing process. In another embodiment, two beads can be attached to a commercially available glove that does not comprise any beads. The glove according to the present invention may be used with a glove donning apparatus comprising one means for detachably retaining the cuff of a glove. Preferably, the glove according to the present invention is used with a glove donning apparatus comprising two means for detachably retaining a glove. In use, the first bead is retained by the inner retaining means and the second bead is retained by the outer retaining means. The beads of the glove can be any suitable shape, for example, square, rectangular, oval, elliptical or circular. The beads may be made from the same material as the glove or a different material. The beads may be made from natural or synthetic rubber, nitrile, silicone, composite, fibre, resin, plastic, elastomer, paper or metal.

Preferably, the glove according to the present invention comprises a first bead positioned at one end of the cuff next to the palm section of the glove and a second bead positioned at the other end of the cuff next to the open end of the glove.

The cuff of the glove retained by the glove retaining means may be held so that substantially the whole of the cuff of the glove is held by the glove retaining means as a result of the cuff being rolled, folded, scrunched or being in layers of rolls. This has the effect of making the glove donning apparatus more compact. Further, this has the effect of opening the glove to a greater extent and positions the finger and thumb portions of the glove more prominently. This makes it easier to align a hand with the finger and thumb portions when donning the glove. This makes the donning process easier, quicker and more reliable.

In the embodiment with two glove retaining formations, substantially the whole of the cuff of the glove is held by the two retaining formations as a result of the cuff being rolled, folded, scrunched, being in layers of rolls or a combination of these. When a glove with two beads is used with the embodiment with two retaining formations, the area of the cuff that is between the two beads is held on the plate in between the two cuff retaining means. This allows easier storage of the cuff portion whilst ensuring that the glove is in an open position. This also makes it easier to insert a hand into the glove as the hand can be inserted straight into the palm section containing the finger and thumb portions without worrying about the cuff portion. The cuff portion will only come into contact with the user's hand once the rest of the glove is in position over the user's hand. This helps to ensure that the external surface of the glove does not come into contact with the user's hand.

The finger and thumb portions of the glove may also be rolled, folded, scrunched, put in layers of rolls or a combination of these. This has the effect of further compacting the apparatus and allowing easier, quicker and more reliable donning of the finger and thumb portions of the glove.

In another embodiment, the plate of the glove donning device further comprises a cover attached to the plate which forms a sealed compartment, and wherein an external surface of the glove is positioned on the interior of the sealed compartment. Further, the whole of the glove may be positioned on the interior of the sealed compartment. The cover may be made of any suitable material. The cover may be a thin membrane, film or other light material. The sealed compartment can be manufactured as an air tight package or vacuum sealed. Preferably, the cover is formed so that it can become detached from the plate when the glove is donned. This may occur as a result of the force provided by the movement of a hand, for example, breaking the seal. Alternatively, the cover may be removed mechanically by an appropriately configured device.

Instead of the cover becoming detached from the plate, the cover itself may split or tear allowing the glove and hand to pass therethrough. This may be achieved by having perforations or lines of weakened material in the cover, or the cover may be sufficiently thin.

A detachable or breakable cover allows the glove to be donned easily without the cover hindering the donning process. It also allows the glove donning apparatus to be more compact but still fully functional as the glove may be contained in a small space.

Preferably, the sealed compartment is sterile. Preferably, the sealed compartment further contains a chemical or active ingredient to ensure the compartment is kept sterile, for example, a disinfectant or anti-bacterial agent formulated to attack and kill bacteria, germs and the like.

In a preferred embodiment the glove may be provided between covers provided on opposing sides of the plate, with the covers and plate co-operating so as to provide a sealed sterile compartment within which the glove is contained until a point immediately prior to donning. It will be appreciated that with the glove mounted to the plate one of the covers faces the exterior surface of the glove, whereas the other of the covers faces the interior surface of the glove. The cover facing the glove interior may be configured do as to be removable prior to donning of the glove.

An object of the embodiment comprising a sterile sealed chamber is to permit the glove to be donned while ensuring that the external surface of the glove remains sterile. Since the apparatus of the present invention is very straightforward to use, there will be a very low risk that the external surface of the glove will be contaminated compared to the prior art gloves and apparatuses.

In yet another embodiment, the plate comprises at least two pieces capable of separating so that the aperture defined by the plate increases in size when the pieces are separated and the cuff of the glove is stretched into a more open position. Preferably, the glove donning apparatus further comprises a means for separating the pieces of the plate. Preferably, the means for separating the pieces of the plate comprises any one of a spring loaded mechanism; extenders; and levers. Preferably, the means for separating the pieces of the plate are controlled by an electronic device.

The advantage of having a plate comprised of at least two pieces is that the glove retaining means can be sized to be only slightly larger than the cuff of the glove. In this way, a small amount of force will be applied to the cuff of the glove when it is mounted onto the glove retaining means and also when the glove is mounted on the plate for a long period of time. This will reduce the possibility of the material from which the glove is made degrading over time, breaking, snapping or becoming weakened. When the glove is ready to be donned, at least two pieces of the plate can be separated to stretch the open end of the glove making it much easier for a hand to be inserted into the glove. This makes the donning process much quicker and easier.

The invention also provides multiple glove donning apparatuses joined together in a roll for use in a dispensing machine.

According to a further aspect of the present invention there is provided a flexible elongate member having a plurality of spaced apertures, each aperture having mounted thereto a glove in a position wherein the finger and thumb apertures of each glove are presented across the aperture, wherein each glove is encapsulated between opposing flexible covers which extend across each aperture such that each glove is retained substantially within the plane of the strip. The covers may comprise flexible films which are adapted to peel from the strip or, alternatively, break to provide access to a glove and to permit the release of a glove from the member. The covers may comprise individual cover members which span each aperture. Alternatively, the covers may be defined by a continuous length of material which extends over the length of a side of the elongate member. The elongate member may be formed into a roll for use within a suitably configured dispenser.

The apertures may be aligned such that their major axis is substantially perpendicular to the longitudinal axis of the elongate member. In an alternative embodiment, the major axis of the apertures may be inclined with respect to the longitudinal axis. The orientation of the aperture axis relative to the elongate member may be used to indicate the size of the gloves carried by the elongate member.

The invention further provides a glove donning apparatus formed into a cartridge for use in a dispensing machine.

The invention provides a glove holding device upon which a glove may be mounted comprising a plate defining an aperture, the plate having a means for detachably retaining a cuff of a glove disposed around the perimeter of the aperture. This glove holding device is designed to be used in combination with a glove to form the glove donning apparatus as described above. Therefore, the glove holding device may have some or all of the additional features associated with the plate of the glove donning apparatus as described above. More specifically, these features may be as follows:

1. the aperture may be sized to allow a hand to pass therethrough;
2. the means for detachably retaining the cuff of a glove may comprise a lip;
3. the lip may comprise a continuous ring, having a circular cross-section, disposed around the perimeter of the aperture;
4. the glove holding device may further comprise a second means for detachably retaining the cuff of a glove;
5. the second means for detachably retaining the cuff of a glove may comprise a lip;
6. the lip being the second cuff retaining means may comprise a continuous ring, having a circular cross-section, disposed around the first cuff retaining means, being at a distance from the first cuff retaining means;
7. the glove holding device may further comprise a cover attached to the plate, said cover being capable of forming a sealed compartment when a glove is mounted on the device so that an external surface of a glove is positioned on the interior of the sealed compartment; and
8. the plate may be comprised of at least two pieces capable of separating so that the aperture defined by the plate increases in size when the pieces are separated.
9. the plate may be comprised of a single piece which does not fully surround the aperture. In such an embodiment, the plate may be considered to be "C" or "U" shaped when viewed in plan.

The invention also provides a method of donning a glove onto a hand using the glove donning apparatus of the invention comprising the steps of
  aligning the fingers and thumb of the hand with the finger and thumb portions of the glove;
  inserting the fingers and thumb of the hand into the finger and thumb portions of the glove; and
  moving the hand through the aperture of the apparatus until the glove becomes detached from the cuff retaining means.

When the plate of the glove donning apparatus comprises at least two pieces capable of separating so that the aperture defined by the plate increases in size when the pieces are separated and the cuff of the glove is stretched into a more open position, the method of donning a glove onto a hand using the glove donning apparatus comprises the steps of:

causing the pieces of the plate to separate thereby stretching the opening of the glove;

aligning the fingers and thumb of the hand with the finger and thumb portions of the glove;

inserting the fingers and thumb of the hand into the finger and thumb portions of the glove; and moving the hand through the aperture of the apparatus until the glove becomes detached from the cuff retaining means.

BRIEF DESCRIPTION OF THE DRAWINGS

The invention will now be described by way of example with reference to the accompanying figures in which:

FIG. 1b shows a cross section through the glove holding device of FIG. 1a;

FIG. 22 shows a cross-sectional view of the glove support of FIG. 21 indicated by arrows A-A of FIG. 21;

FIG. 23 shows a cross-sectional view of the glove support and a glove;

DETAILED DESCRIPTION OF EXEMPLARY EMBODIMENTS

Figure 1A:
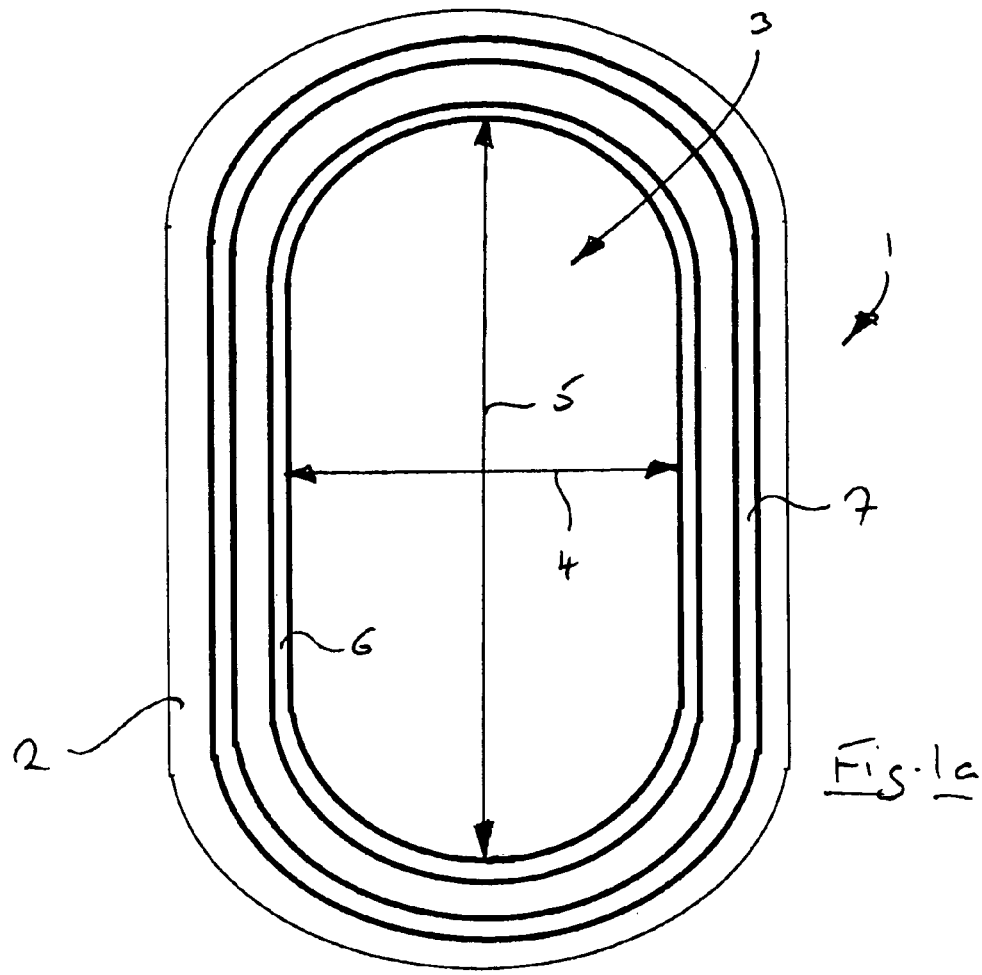
FIG. 1a shows a top view of a glove holding device.
Figure 1B:
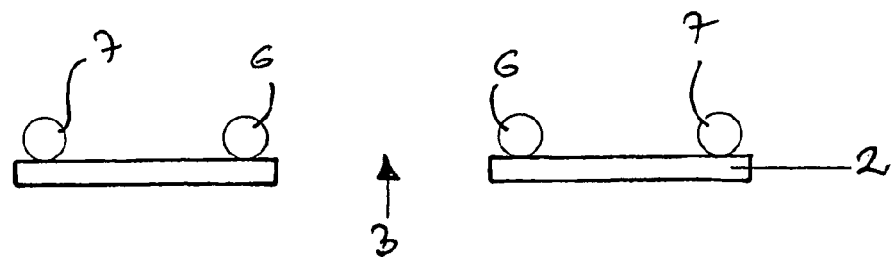
Figure 12:
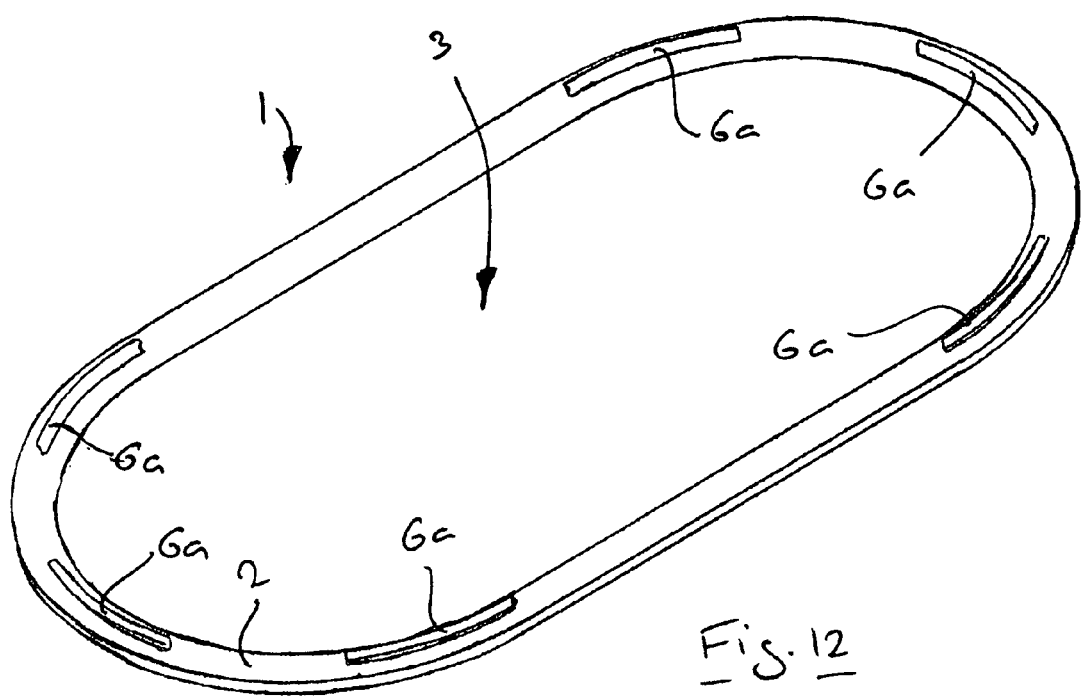
FIG. 12 shows a perspective view of an alternative embodiment of a glove holding device.
Figure 13:
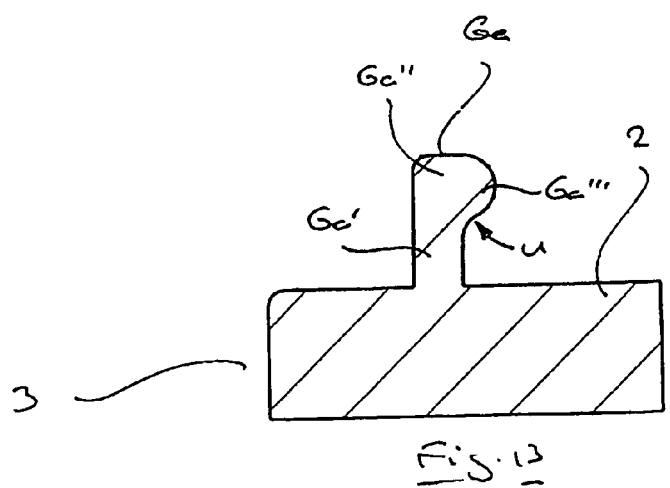
FIG. 13 shows a cross-sectional view of a portion of the glove holding device of FIG. 12.

FIG. 1a shows the design of a glove holding device 1. This device 1 comprises a plate 2 defining an aperture 3 which is a rounded rectangular opening of 70 mm in width 4 and 130 mm in length 5 and large enough for a hand to pass through the aperture to don a glove. These dimensions can vary to suit the size of the hand. The plate is fitted with two lips, an inner lip 6 and an outer lip 7. The two lips are at a distance of about 4 mm from each other. This distance can vary from 0.5 mm to 10 mm or more. FIG. 1b shows a cross section through the glove holding device of FIG. 1a. The lips 6,7 are shown to be substantially circular in cross-section. It will be understood that the lips 6,7 may be shaped so as to exert a required grip on the glove. Referring now to FIGS. 12 and 13 there is shown an alternative embodiment of the device 1. Features common to the device described with reference to FIG. 1 are identified with like reference numerals. The plate 2 is provided with a single discontinuous rib having a number of spaced lip sections 6a. A single discontinuous lip of this type may be suitable for use with gloves manufactured from certain materials, whereas the twin continuous lip arrangement of FIGS. 1 and 2 may be suitable for other glove materials. FIG. 13 shows a cross-sectional view of the plate 2 and lip 6a. The lip 6a has a base portion 6a' which extends from the plate 2 and which is surmounted by a top portion 6a". The top portion has a rounded nose 6a''' which extends outwardly with respect to the plate aperture 3. The nose 6a''' and base portion 6a" of the lip 6a co-operate to form an undercut U of the lip 6a which assists in retaining a glove to the plate 2. It will be appreciated that the cross-sectional form of the lip 6a may be incorporated into one or both of the lips 6,7 of the plate 2 of FIG. 1.

Figure 2:
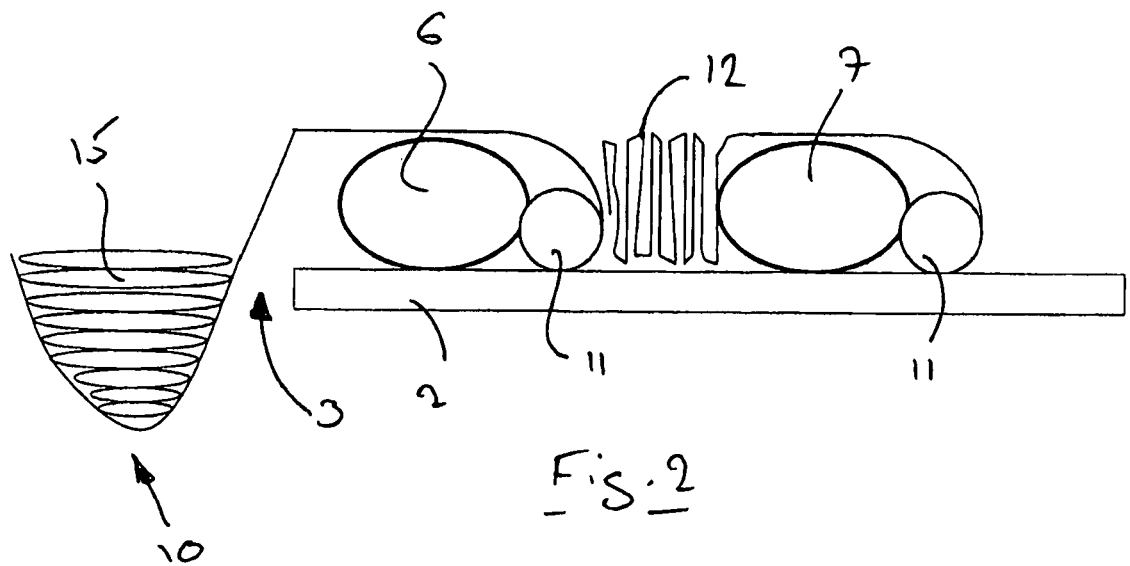
FIG. 2 shows a cross section through part of a glove donning apparatus.

FIG. 2 shows part of a glove 10 with two beads 11 which are held or stretched over an inner lip 6 and an outer lip 7. In between the two beads 11 is a cuff section 12 of the glove which is folded. The folds of the cuff section 12 are retained in a gap between the inner lip 6 and the outer lip 7. The glove section beyond beads 11 and folds 12 extends into the aperture 3 of the plate 2. The fingers 15 of the glove (only one shown) are folded.

Figure 3:
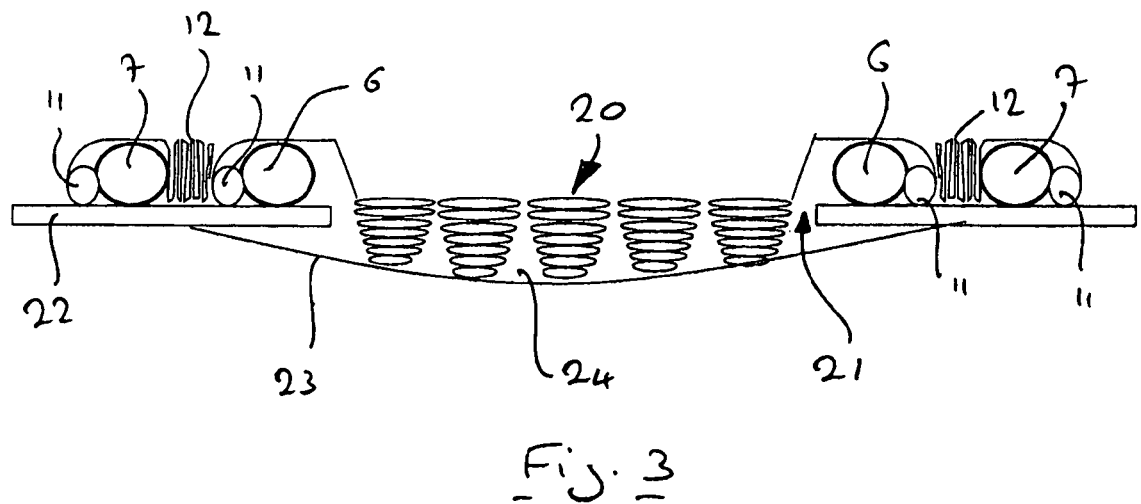
FIG. 3 shows a cross section through a glove donning apparatus wherein the apparatus comprises a cover which forms a sealed compartment.

FIG. 3 shows a glove donning apparatus wherein the apparatus comprises a cover 23 which forms a sealed compartment 24. The open end of a glove 20 is stretched open across an aperture 21 of a plate 22. The finger and thumb portions of the glove 20 are folded. The cover 23 is attached to the plate 22 and forms a sealed compartment 24 wherein the external surface of the glove 20 is positioned on the interior of the sealed compartment 24. When the fingers and thumb of a hand are inserted into the finger and thumb portions of the glove 20, exerting pressure on the cover 23, the cover 23 either becomes detached from the plate 22 or splits or tears to allow the hand to be fully inserted into the glove.

Figure 4:
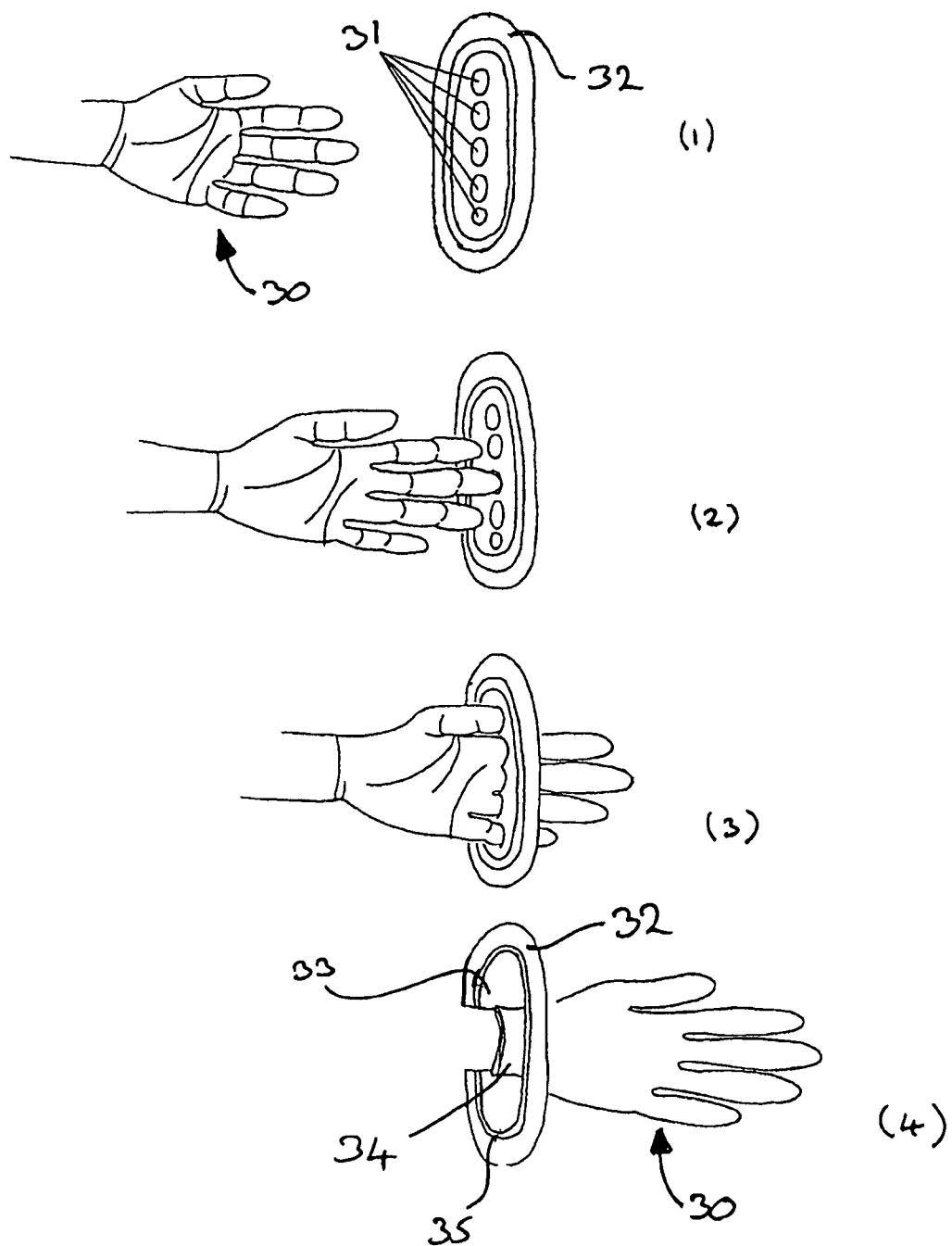
FIG. 4 shows a method of donning a glove onto a hand.

FIG. 4 shows a method of donning a glove 31 onto a hand 30. The hand 30 is aligned and moved towards the finger and thumb openings of the glove 31 (FIGS. 4(1) and 4(2)). The hand 30 is then continuously moved forward through the open end of the glove that is stretched open over an aperture of a plate 32, thereby inserting the fingers and thumb into the finger and thumb portions of the glove (FIG. 4(3)). Once the hand is inserted far enough through the aperture 33 in the plate 32 so that the glove is virtually entirely donned, a cuff 34 of the glove will become detached from a cuff retaining means 35 thus completing the donning, of the glove 30 (FIG. 4(4)). The hand can then be removed from the aperture 33 in the plate 32. The force exerted by the hand movement is sufficient to break a cover, if a cover is attached. The above described steps may be repeated so as to don a further glove to the hand of a wearer where double gloving is deemed necessary.

Figure 5:
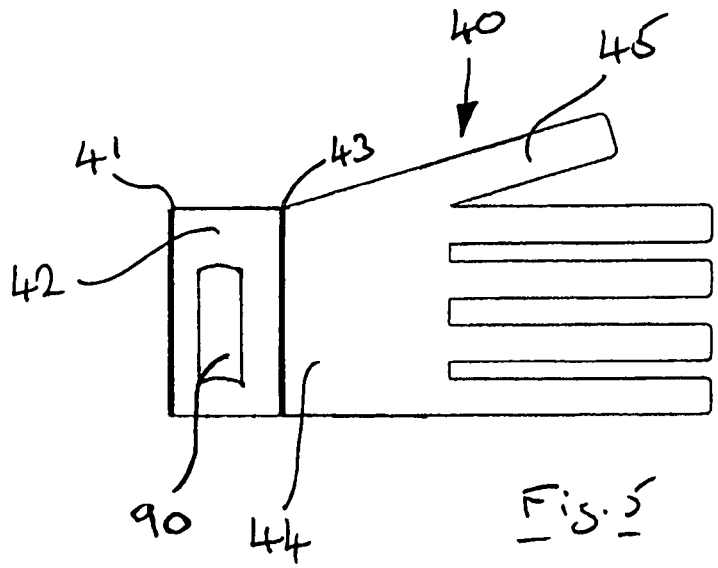
FIG. 5 shows a glove comprising two beads.

FIG. 5 shows the design of a glove 40 comprising two beads. One bead 41 is positioned on the cuff 42 of the glove 40 around the open end of the glove 40. The other bead 43 is positioned just above a palm portion 44 of the glove 40 and also just above where a thumb portion 45 of the glove 40 connects to the palm portion 44 of the glove. The cuff 42 may optionally be provided with an external pocket generally designated 90. The pocket 90 is configured so as to be able to receive and retain a tongue like projection of a glove removal apparatus. Such an apparatus may be used by a wearer of the glove 40 to remove the glove 40 without touching the glove 40. In use, the projection of the removal apparatus is inserted into the pocket 90. The wearer is then able to remove their hand from the glove 40 such that the glove 40 remains attached to the projection.

Figure 6:
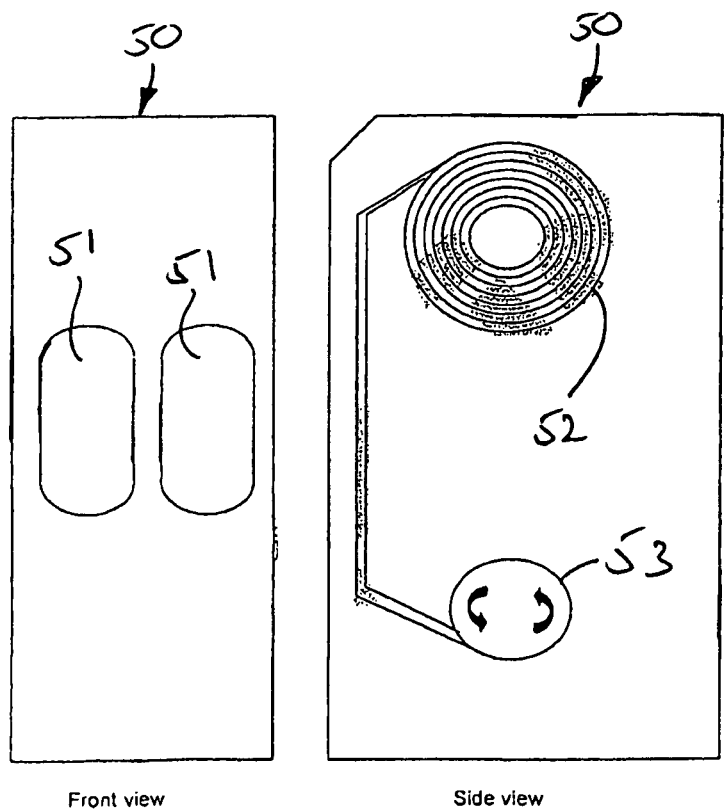
FIG. 6 shows a roll of glove donning apparatuses contained within a glove dispensing machine.

FIG. 6 shows a roll of glove donning apparatuses contained within a glove dispensing machine 50. The glove dispensing machine 50 has an opening 51 for each hand. A large number of glove donning apparatuses joined together in sheet form are rolled onto a dispensing roll 52 and are enclosed in the glove dispensing machine 50. A receiving portion 53 collects the glove holding devices once the gloves have been detached therefrom. The glove dispensing machine 50 can have a number of designs, for example, a manually operated mechanical design, or an electrically operated design. This may be dictated by cost.

Figure 7:
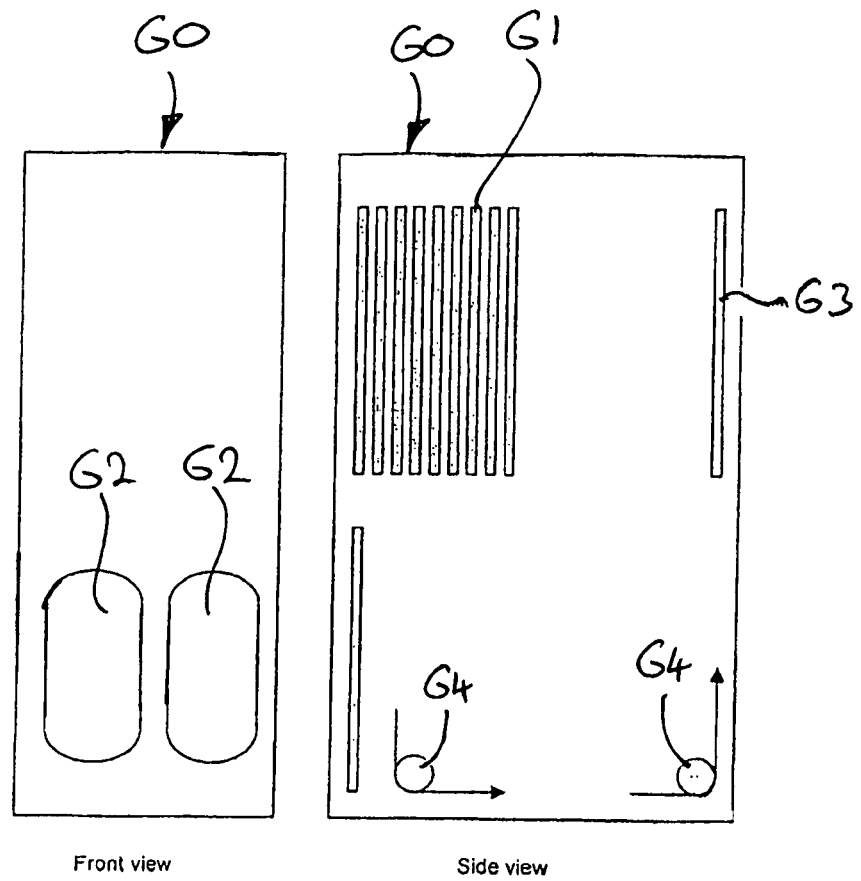
FIG. 7 shows cartridges formed from glove donning apparatuses contained within a glove dispensing machine.

FIG. 7 shows cartridges 61, formed from glove donning apparatuses, contained within a glove dispensing machine 60. Cartridges 61, comprising two glove donning apparatuses, are loaded into the glove dispensing machine 60. Gloves are donned at two openings in the dispensing machine 62. The empty cartridge 63 is then taken away by a transporting mechanism 64. The glove dispensing machine 60 can have a number of designs, for example, a manually operated mechanical design, or an electronically operated design. This may be dictated by cost.

Figure 8:
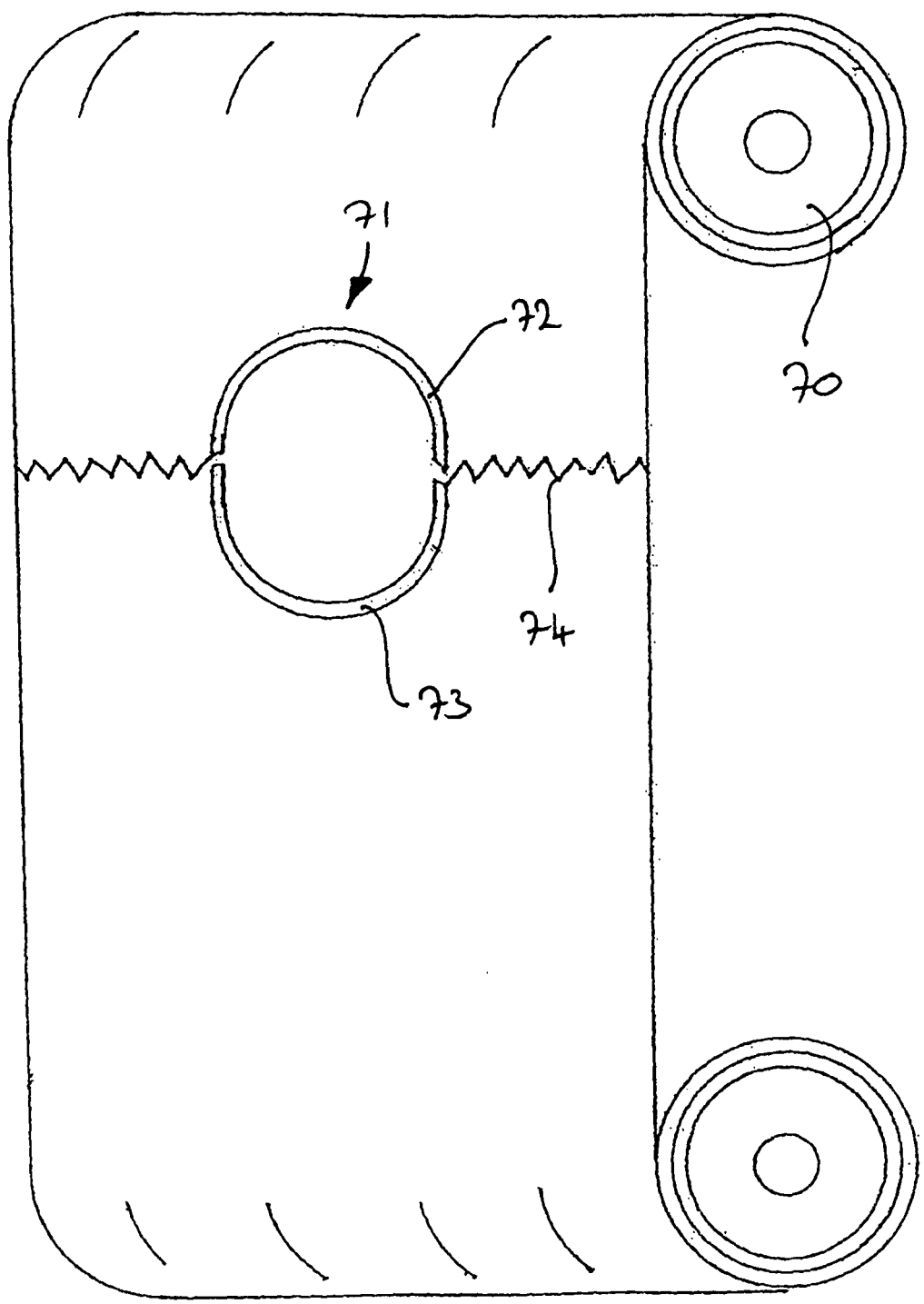
FIG. 8 shows a roll of glove holding devices, wherein the plate of the glove holding device comprises two pieces.
Figure 9:
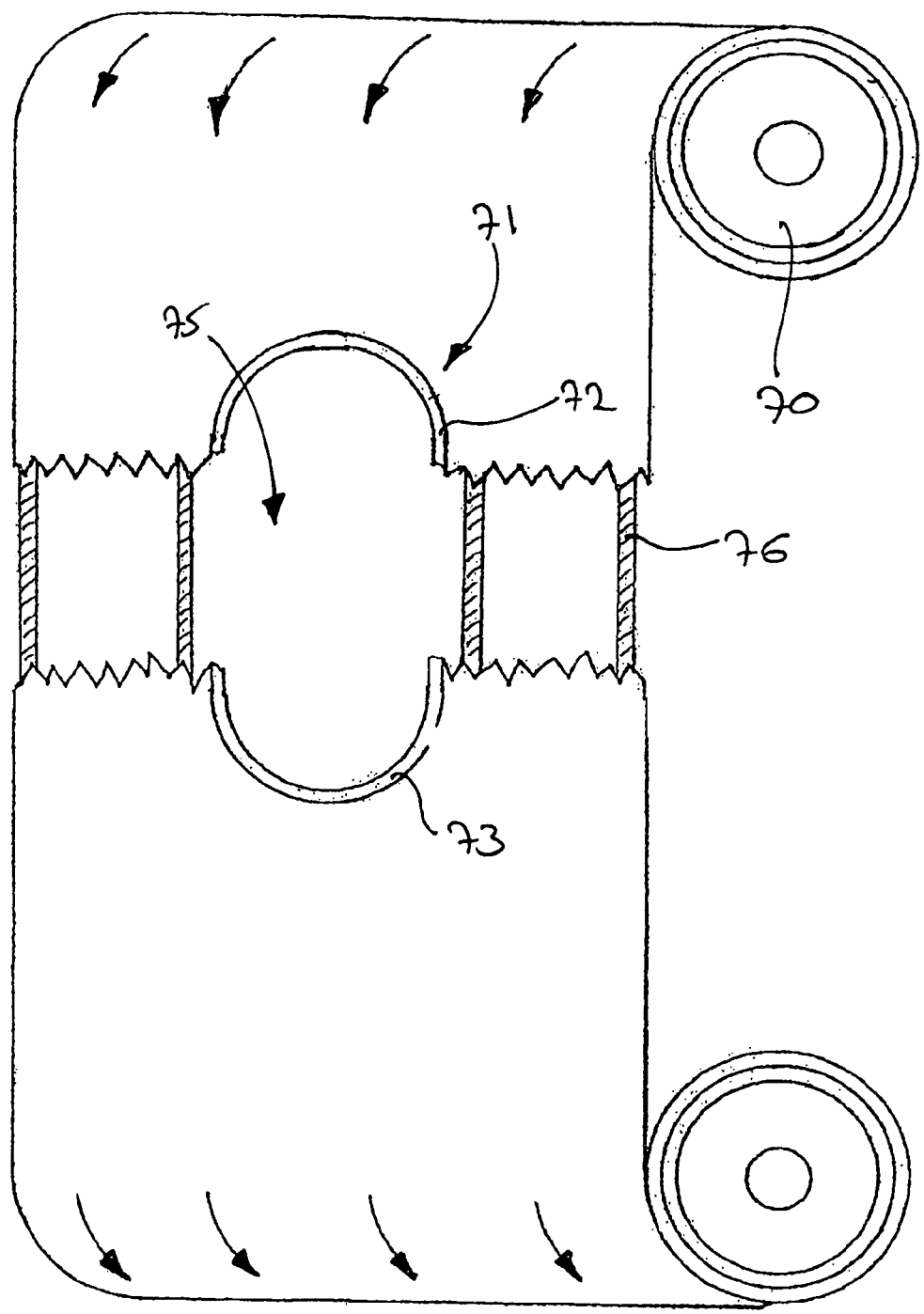
FIG. 9 shows a roll of glove holding devices, wherein the plate of the glove holding device comprises two pieces and the two pieces have been separated.

FIG. 8 shows a roll 70 of glove holding devices, wherein a plate 71 of a glove holding device comprises an upper piece 72 and a lower piece 73. There is a perforated line 74 in the roll 70 along which the roll can separate. When the roll separates along the perforated line 74, as shown in FIG. 9, the upper piece 72 of the plate separates from the lower piece 73 of the plate, thereby increasing the size of an aperture 75. The roll 70 does not completely separate as it is held together by four flexible holding straps 76.

Figure 10:
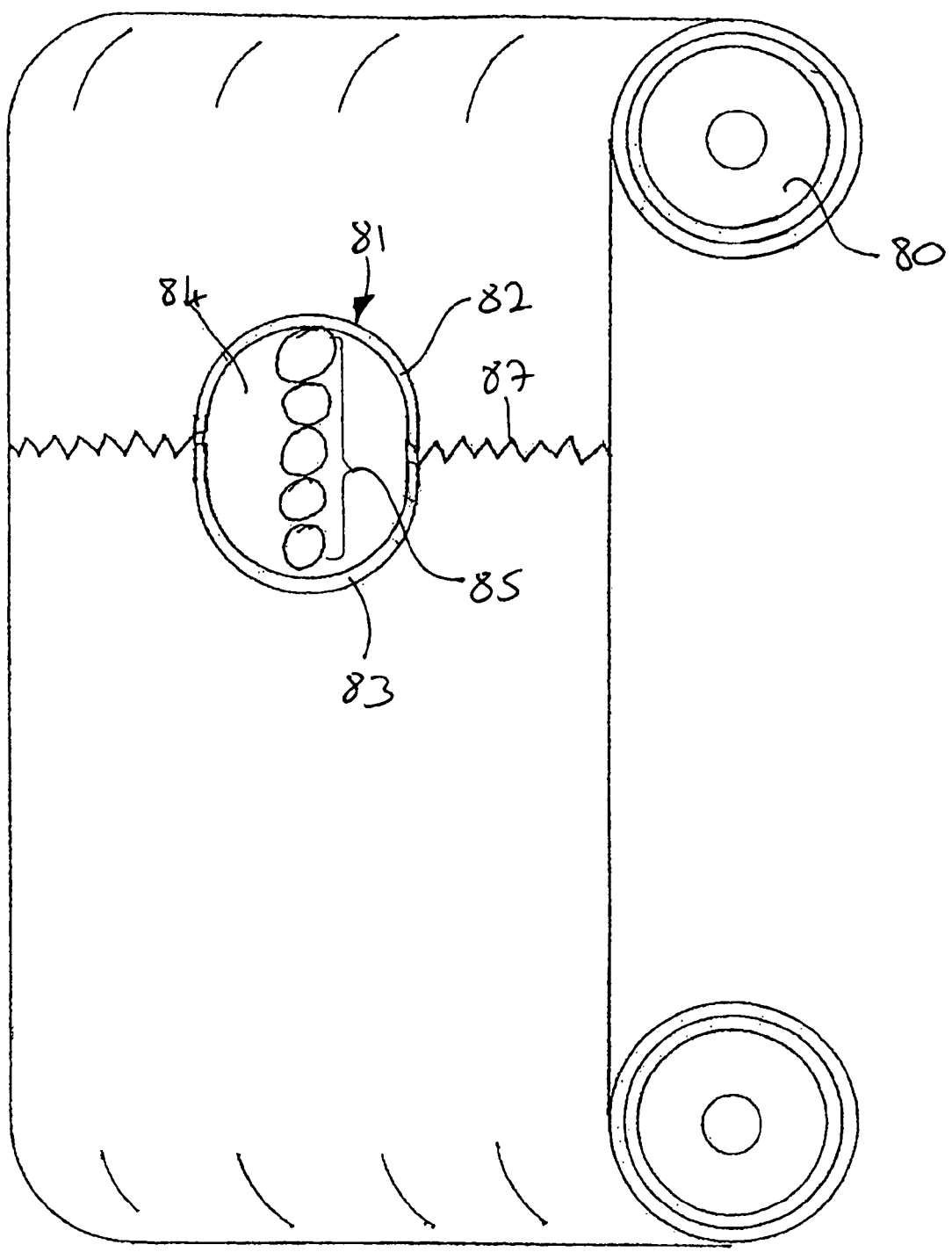
FIG. 10 shows a roll of glove donning apparatuses, wherein the plate of the glove donning apparatus comprises two pieces.
Figure 11:
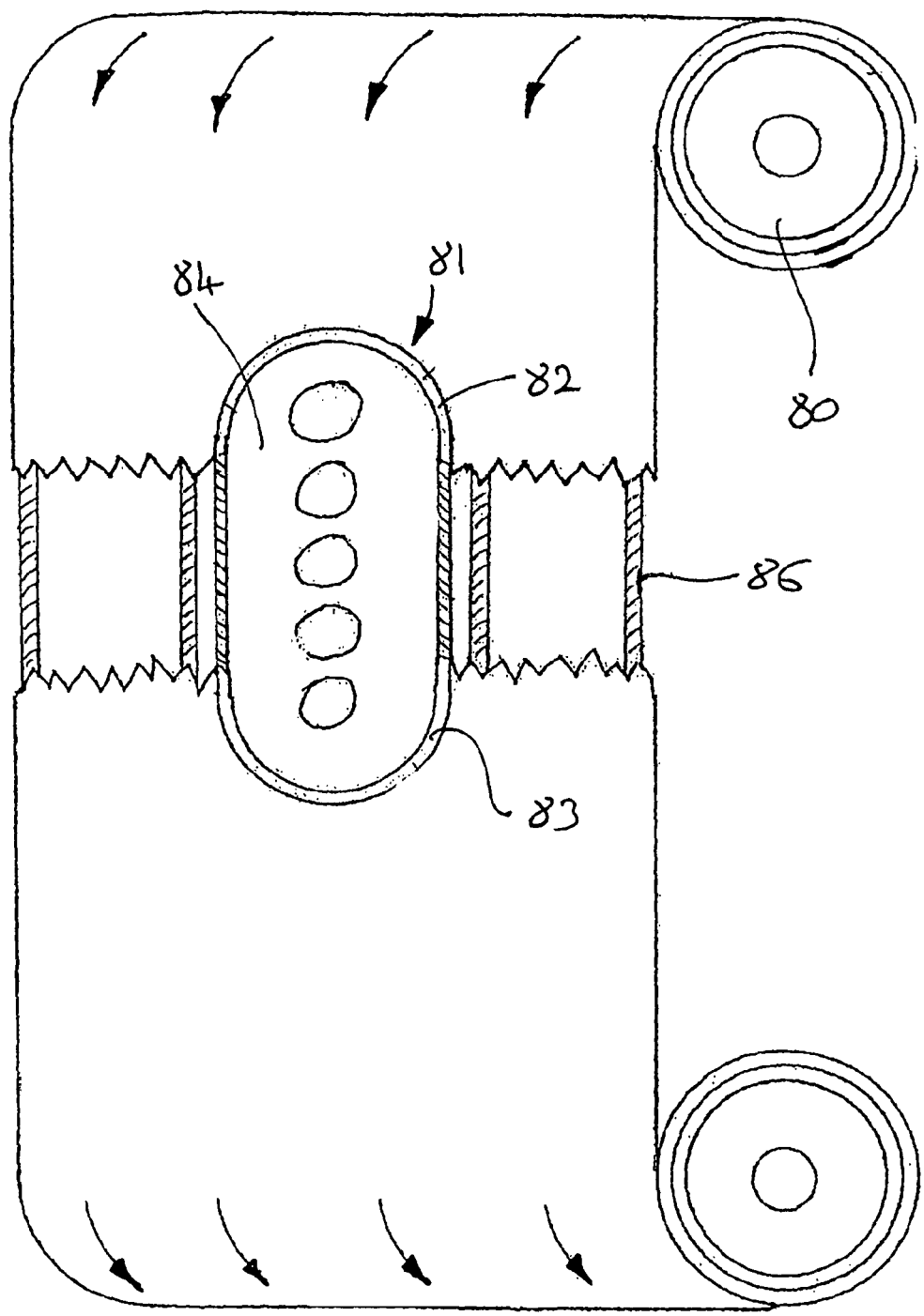
FIG. 11 shows a roll of glove donning apparatuses, wherein the plate of the glove donning apparatus comprises two pieces and the two pieces have been separated.

The effect that this separation in the plate has on a glove mounted on the glove holding device is shown in FIGS. 10 and 11. FIG. 10 shows a roll 80 of glove donning apparatuses, wherein a plate 81 of the glove donning apparatus comprises an upper piece 82 and a lower piece 83. A glove 84 is mounted on the plate 81 across an aperture defined by the plate 81. Finger portions 85 of the glove 84 can be seen. There is a perforated line 87 in the roll along which the roll can separate. When the roll 80 separates along the perforated line 87, as shown in FIG. 11, the upper piece 82 of the plate 81 separates from the lower piece 83 of the plate, thereby increasing the size of the aperture defined by the plate 81 and thus stretching the open end of the glove 84 mounted on the plate 81. This has the effect of stretching the open end of the glove 84 into a more open position which makes it easier to insert a hand into the glove during the donning process. The roll 80 does not completely separate, once the glove has been donned and therefore removed from the plate 81, because it is held together by four flexible holding straps 86. The above described separation feature may be embodied in an individual glove holding device of the type described with reference to FIG. 1a.

Figure 14:
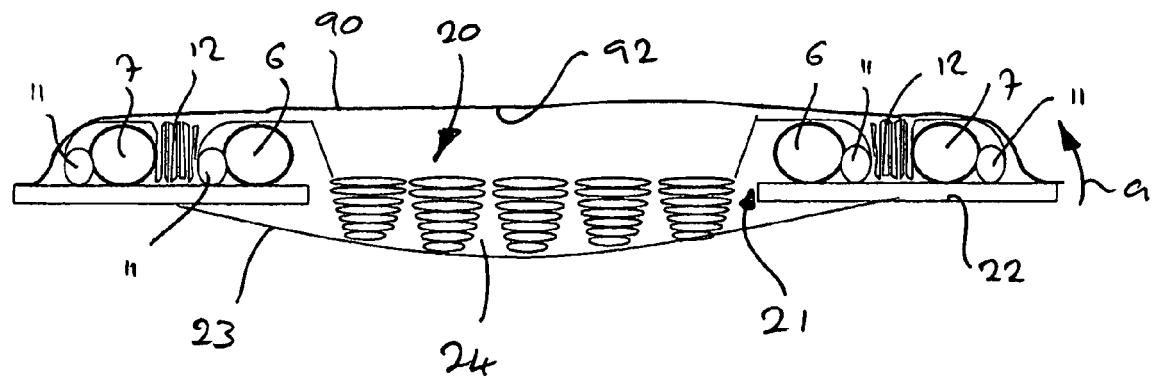
FIG. 14 shows a cross section through a glove donning apparatus wherein the apparatus includes covers provided on either side of the apparatus which form a sealed compartment containing the glove.

Referring now to FIG. 14 there is shown a glove donning apparatus similar to that shown in FIG. 3. Features common to the embodiment described with reference to FIG. 3 are identified with like reference numerals. As before, the glove 20 is provided across the aperture 21 of the plate 22 with the finger and thumb portions of the glove presented. The finger and thumb portions are concertinaed by the cover 23 such that the glove 20 is contained substantially in the plane of the plate 22.

The apparatus is provided with an additional cover 90 which overlies the plate 22 and glove 20. The additional cover 90 is provided on the opposite side of the plate 22 to the first cover 23 such that the glove 20 is encapsulated between both covers 23,90. The inner side 92 of the additional cover 90, which is to say the side of the additional cover 90 facing the glove 20, may be provided with an adhesive so as to enable the additional cover 90 to attach to the plate 22 around the periphery of the glove 20 and there by provide a hermetic seal. Alternatively, the additional cover 90 may be connected to the plate 22 in an alternative manner, for example by a welding operation. It will be appreciated that both covers 23,90 serve to maintain the sterility of the glove up until the point it is donned by a user.

Prior to the donning of the glove 20 by a user, the additional cover 90 may be removed so as to provided unimpeded access by the user to the glove 20. The additional cover 90 may be peeled from the plate 22 as indicated by arrow 94. Alternatively, the additional cover 90 may be adapted so as to tear or break in the same manner as the first cover 23 by the action of a user moving their fingers into the glove finger and thumb portions.

The plate 22 to which the glove 20 is mounted may comprise an elongate member having a plurality of space apertures 21 to which individual gloves 20 are mounted. The elongate member may preferably be formed from a flexible material such that the member and gloves carried thereby may be formed into a roll. In such an embodiment the additional cover 90 may be defined by a continuous film or strip aligned with the apertured elongate member.

Figure 15:
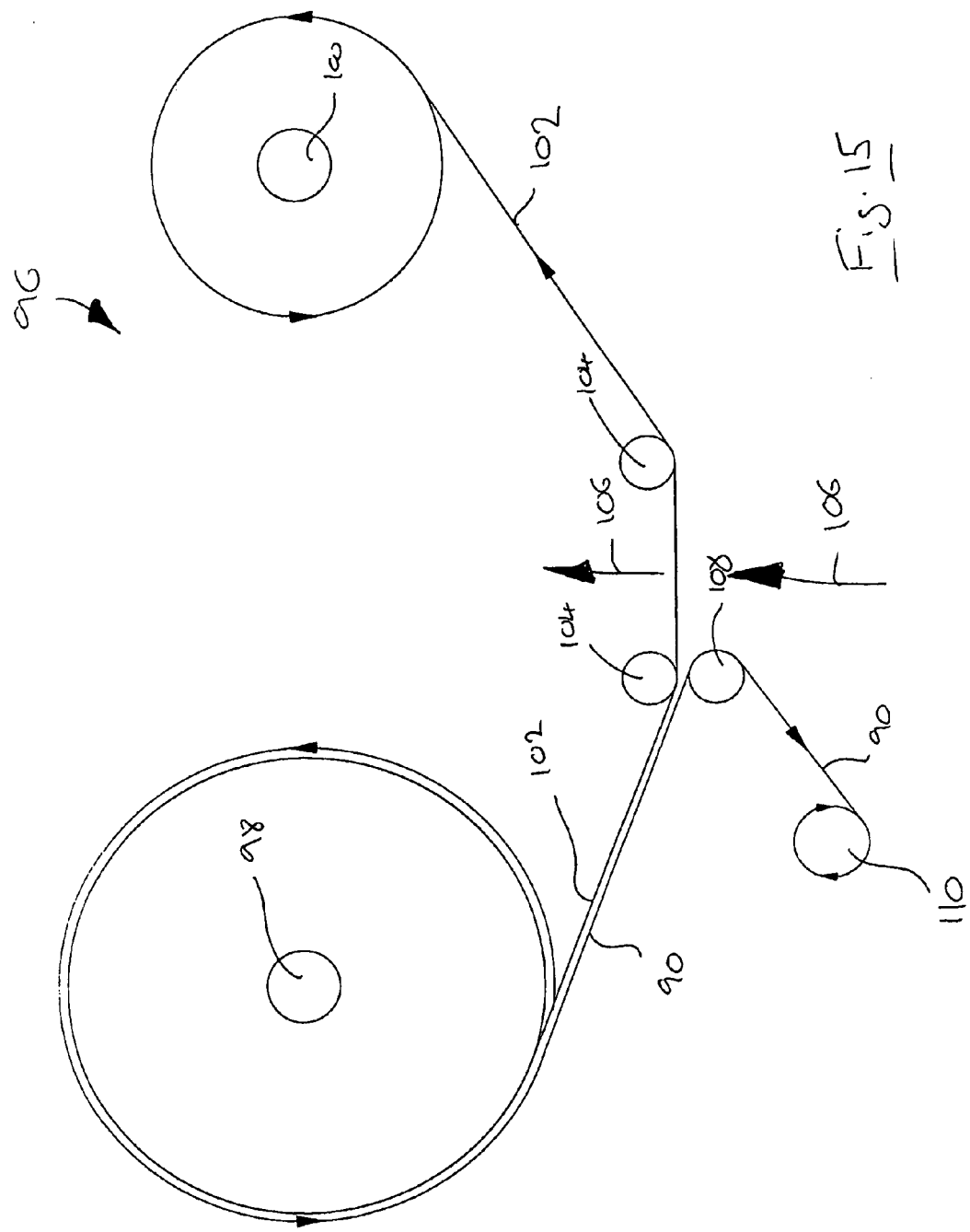
FIG. 15 shows a schematic top plan view of a glove dispensing and donning apparatus.

FIG. 15 shows a schematic plan view of an apparatus generally designated 96 which is configured for use with an elongate member of the type described above. It will be appreciated that in use the apparatus is provided within a casing. The apparatus comprises feed and collection rollers 98, 100 which accommodate an apertured strip 102 of the type described above. The feed roller 98 carries a rolled portion of the strip 102 having unused gloves mounted thereto. The collection roller 100 carries a rolled portion of the strip from which gloves have been released. Between the feed and collection rollers 98,100, there are provided a pair of idler rollers 104 which serve to present a portion of the strip 102 having a glove mounted thereto to a user in a position which facilitates donning of the glove as indicated by arrows 106. The idler rollers 104 are positioned in the vicinity of a hand insertion aperture of the casing and furthermore provide a means to resist movement of the strip 102 away from the user during the donning process. The apparatus 96 is further provided with a pair of rollers 108,110 which act to separate the additional cover 90 from the strip 102 and subsequently collect the cover 90. The additional cover 90 is removed from the strip 102 immediately prior to the idler rollers 104 thereby maintaining the sterility of individual gloves up until the point of donning of a glove.

Figure 16:
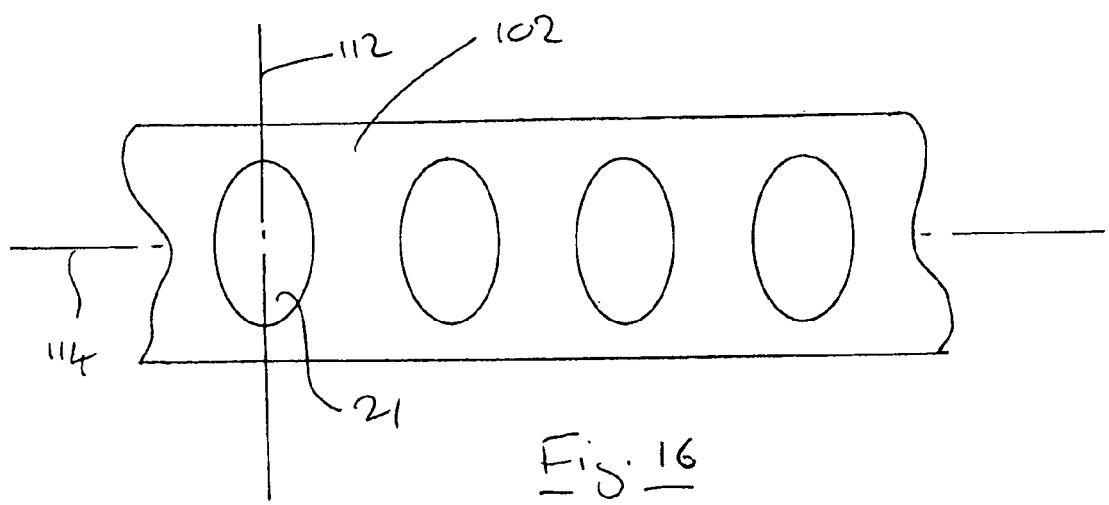
FIGS. 16 and 17 show plan views of glove carrying strips.
Figure 17:
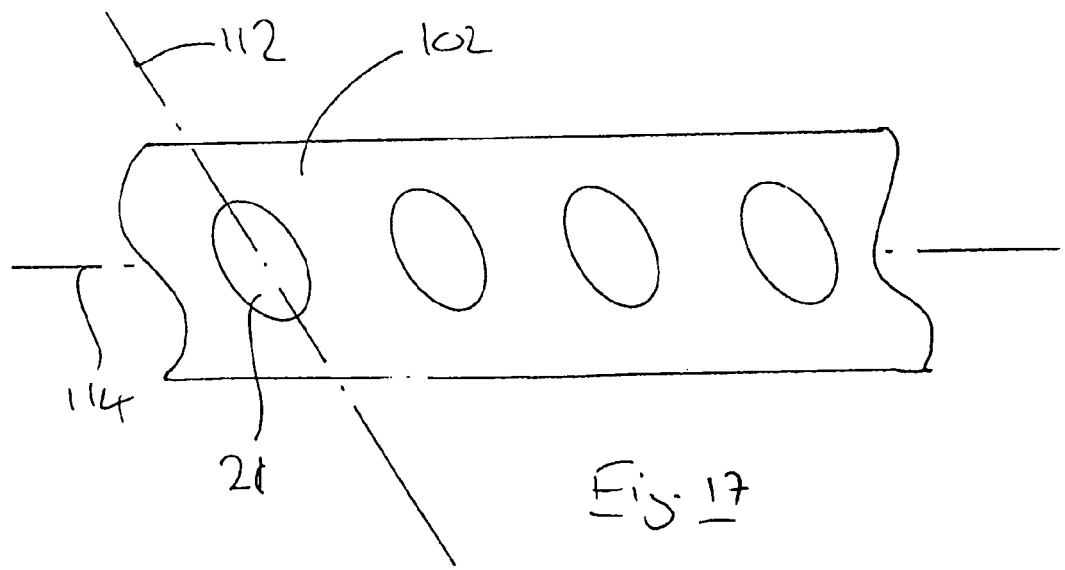

FIGS. 16 and 17 show plan views of glove carrying strips 102. In FIG. 15 the major axis 112 of each aperture 21 is aligned substantially perpendicularly to the longitudinal axis 114 of the strip 102. In FIG. 16 the major axis 112 of each aperture 21 is inclined with respect to the major axis 114 of the strip. The orientation of the aperture 21 with respect to the strip 21 may be used to indicate differing aperture 21 sizes and hence different glove sizes carried by a strip 102. For example, the orientation shown in FIG. 15 may be used in conjunction with medium sized gloves, whereas the orientation shown in FIG. 16 may be used in conjunction with small sized gloves. So as to accommodate differing glove sizes and hence different strip configurations, a glove dispensing apparatus of the type described above for use with strips 102 of this type may be adapted accordingly. For example, the apparatus may be provided with differing sets of feed, collection and idler rollers. For example, the rollers for strips of the type shown in FIG. 16 may be inclined within the dispenser casing such that the strip apertures 21, and hence gloves 20, are presented with their major axis 112 in a substantially vertical manner to the user.

Figure 18:
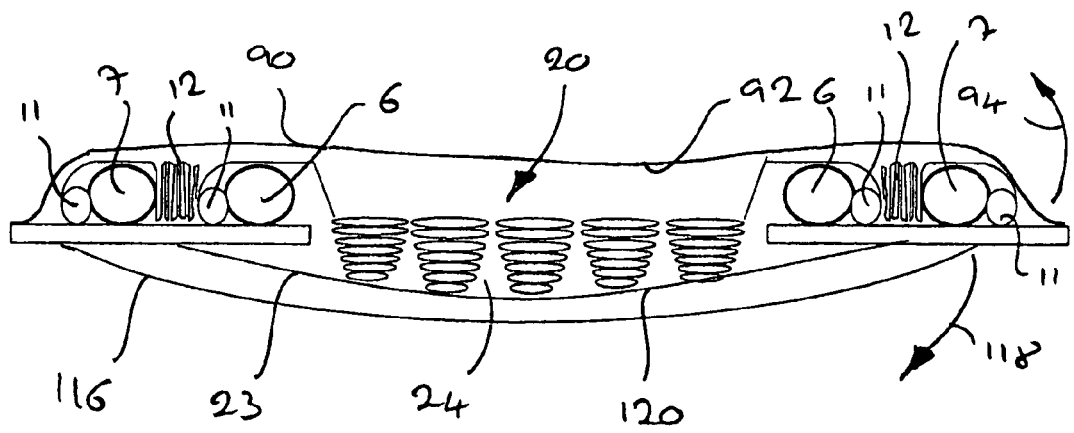
FIG. 18 shows a cross-sectional view through a glove donning apparatus similar to that shown in FIG. 14 but with an additional cover.

Referring now to FIG. 18 there is shown a glove donning apparatus similar to that shown in FIG. 14. Features common to the embodiment described with reference to FIG. 14 are identified with like reference numerals. As before, the glove 20 is provided across the aperture 21 of the plate 22 with the finger and thumb portions of the glove presented. The finger and thumb portions are folded in concertina like manner by the cover 23 such that the glove 20 is contained substantially in the plane of the plate 22.

The apparatus is provided with an additional cover 90 which overlies the plate 22 and glove 20. The additional cover 90 is provided on the opposite side of the plate 22 to the first cover 23 such that the glove 22 is encapsulated between both covers 23,90. The inner side 92 of the additional cover 90, which is to say the side of the additional cover 90 facing the glove 20, may be provided with an adhesive so as to enable the additional cover 90 to attach to the plate 22 around the periphery of the glove 20 and there by provide a hermetic seal. Alternatively, the additional cover 90 may be connected to the plate 22 in an alternative manner, for example by a welding operation. It will be appreciated that both covers 23,90 serve to maintain the sterility of the glove 20 up until the point it is donned by a user.

The apparatus is provided with a third cover 116. The third cover 116 is provided on the opposite side of the plate 22 to the additional cover 90 and overlies the first cover 23. The purpose of the third cover 116 is to protect the exterior face 120 of the first cover and hence maintain the sterility thereof. It has been observed that during the action of a user donning a glove 20 and withdrawing their gloved hand through the plate aperture 21, the outer surface of the glove 20 can come into contact with the outer surface 120 of the now broken first cover 23. In the event that the outer surface 120 of the first cover is non sterile, then the sterility of the glove 20 may be compromised. The third cover 116 thus defines with the first cover 23 and plate 22 a further sterile compartment. As with the additional cover 90, the inner side of the third cover 116, which is to say the side of the third cover 116 facing the plate 22, may be provided with an adhesive so as to enable the third cover to attach to the plate 22 around the periphery of the first cover 23. Alternatively, the third cover 116 may be connected to the plate 22 in an alternative manner, for example by a welding operation.

Prior to the donning of the glove 20 by a user, both the additional cover 90 and the third cover 116 may be removed so as to provided unimpeded access by the user to the glove 20. The additional cover 90 may be peeled from the plate 22 as indicated by arrow 94. Alternatively, the additional cover 90 may be adapted so as to tear or break in the same manner as the first cover 23 by the action of a user moving their fingers into the glove finger and thumb portions. The third cover is preferably peelable from the plate 22 as indicated by arrow 118.

Figure 19:
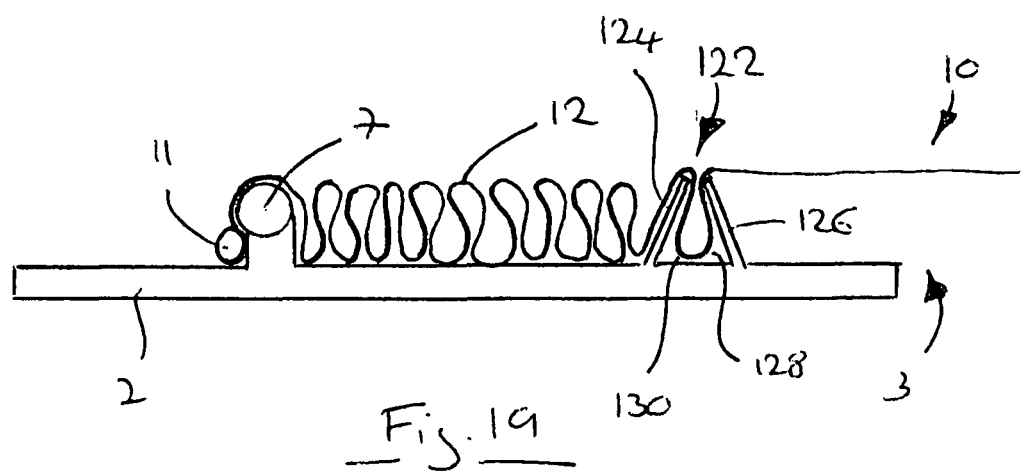
FIG. 19 shows a partial cross-sectional view through a glove donning apparatus according to a further embodiment of the present invention.

FIG. 19 shows a further embodiment of a glove donning apparatus similar to that shown in FIG. 2. Features common to the embodiment of FIG. 2 are identified with like reference numerals. The apparatus differs in that firstly, the inner lip 6 has been replaced by a gripping arrangement generally designated 122, and secondly by the omission of the second, inner bead 11 of the cuff section of the glove 10. It will be appreciated that the glove 10 thus has a more conventional configuration and that the plate 2 is thus adapted to receive and retain such conventionally configured gloves 10. The gripping arrangement 122 comprises opposed resilient projections 124,126 which extend from the plate 2. In the embodiment shown, the projections 124,126 are inclined towards one another so as to define a cavity 128 between their inner faces and the plate 2. In use, a loop 130 of glove cuff material can be inserted into the cavity 128 and gripped between the opposed distal ends of the projections 124,126. The portion of the glove cuff which forms the loop 130 may be thickened so as to resist the forces imposed thereupon by the projections 124,126.

In an alternative embodiment the outer lip 7 may be replaced by a similar gripping arrangement. The or each gripping arrangement may extend continuously around the plate aperture 3. Alternatively, the or each gripping arrangement may extend around the plate aperture 3 in a discontinuous manner. Although not shown, the apparatus of FIG. 20 may be provided with one or more of the aforementioned cover arrangements 23,90,116.

Figure 20:
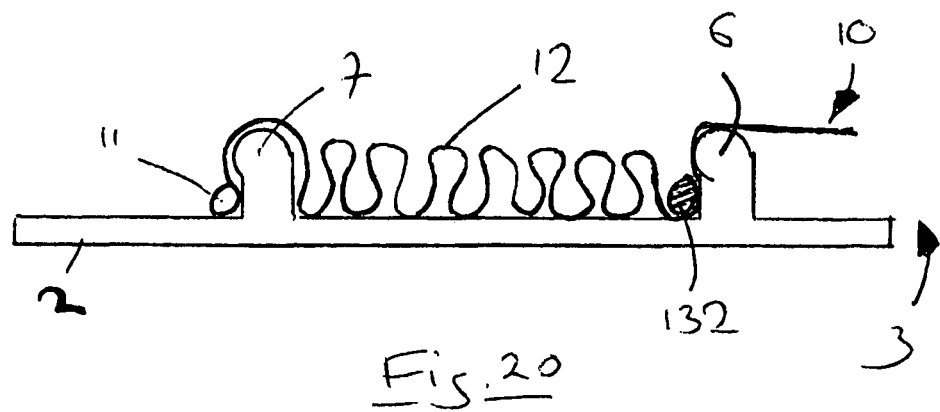
FIG. 20 shows a partial cross-sectional view through a glove donning apparatus according to a further embodiment of the present invention.

FIG. 20 shows a further embodiment of a glove donning apparatus similar to that shown in FIGS. 2 and 19. Features common to the embodiments of FIGS. 2 and 19 are identified with like reference numerals. The inner lip 6 is retained and the glove 10 retained thereto be a breakable retainer 132. It will be understood that the retainer 132 extends in a loop around the inner lip and is broken by the action of a user donning the glove 10 to release the glove cuff from the inner lip 6. The apparatus of FIG. 21 thus illustrates another way in which a conventionally configured glove 10 not having a second bead may be used in conjunction with the plate 12.

Figure 21:
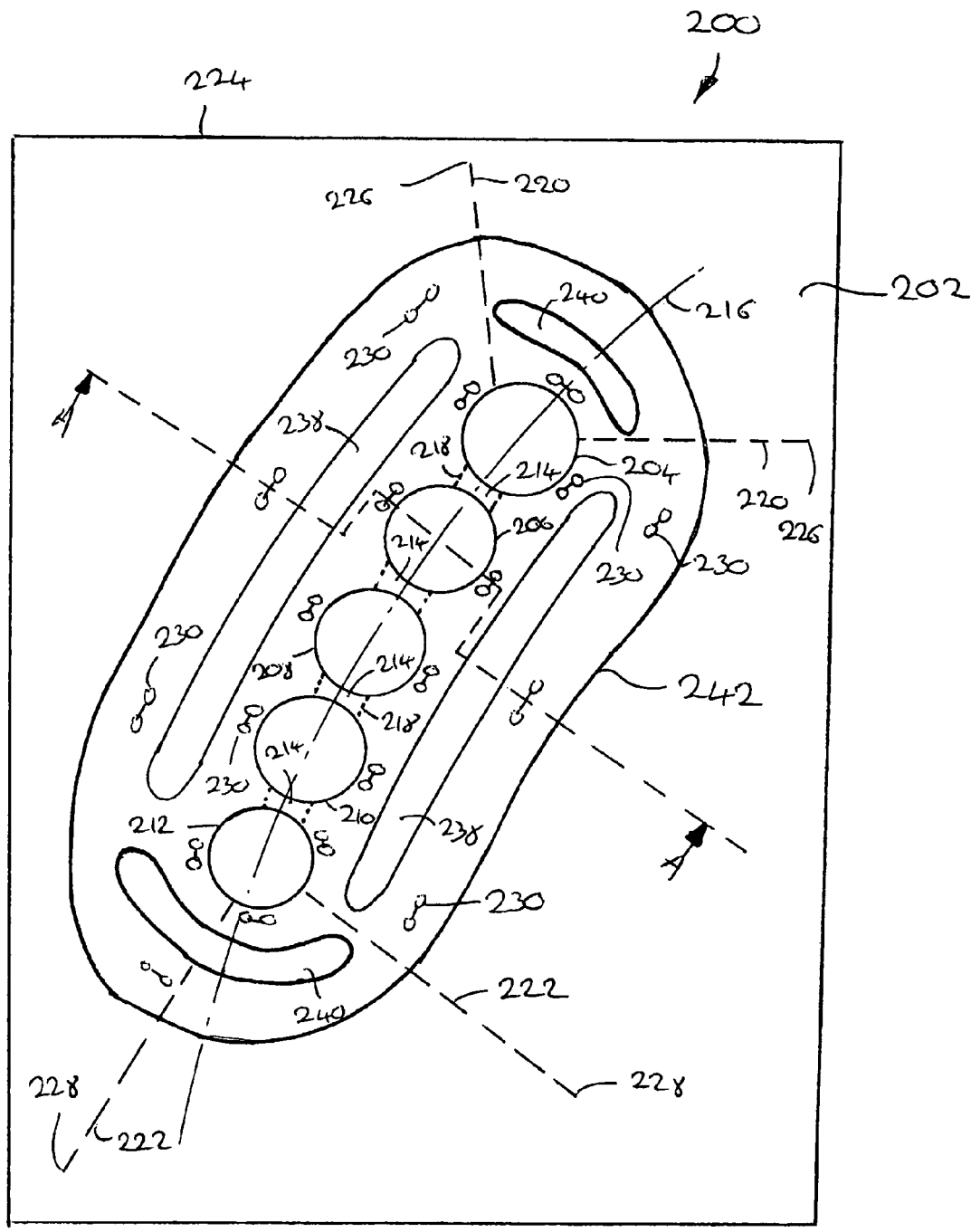
FIG. 21 shows a plan view of a glove support according to a further embodiment of the present invention.

FIGS. 21 and 22 show a glove support generally designated 200. The support has a front side which, in use, faces towards a user and a rear side which, in use, faces away from the user. The support 200 comprises a sheet 202 of flexible material such as, for example, PVC, Polypropylene or Poly styrene having a thickness of, for example, 0.01 mm to 0.5 mm. It will be appreciated that the material and thickness thereof will depend to a certain extent upon the material and configuration of the glove intended to be mounted to the support 200. The cross-sectional view of FIG. 23 exaggerates the thickness of the sheet for the purpose of explaining the features and functions of the support 200. The support 200 includes a plurality of digit apertures comprising a thumb aperture 204, index finger aperture 206, middle finger aperture 208, ring finger aperture 210 and little finger aperture 212. In the embodiment shown the support is arranged to receive the left hand of a user with the thumb aperture 204 uppermost and the little finger aperture 212 lowermost. In the embodiment shown, the digit apertures 204, 206, 208, 210, 212 are separated from one another with a web 214 being provided between adjacent apertures. In an alternative embodiment the spacing of the digit apertures may be such that two or more of the aperture overlap to define an aperture configured to receive two or more digits therethrough. The apertures 204, 206, 208, 210, 212 are arranged along a curved path 216.

The curve of the path 216 takes into account both the material characteristics of the glove and the orientation of the hand of the user. A glove, when mounted to the support must not be held in a position which could weaken the material of the glove, for example by sustained stretching over lime. The orientation of the apertures 204, 206, 208, 210, 212 should also conform as far as possible to a relaxed position of the hand of the user so as not to require the user to place their hand in an awkward and/or uncomfortable position when donning a glove.

The webs 214 are provided with lines of weakness 218 which extend between adjacent digit apertures. The lines of weakness 218 are provided so that the webs 214 are able to break as will be described in greater detail below. The lines of weakness 218 may be defined by, for example, perforations or scoring. Alternatively, the webs 214 may be adapted to break by other means. For example, the thickness on the support sheet 202 in the region of the webs 214 may be thinner that the remainder of the sheet 202. Alternatively the sheet material in the vicinity of the webs 214 may be treated so as to be liable to break or fracture.

Further lines of weakness 220,222 extend from the thumb and little finger apertures 204,212 respectively. As before these lines of weakness 220,222 may be defined by perforations or scoring. The lines of weakness 220,222 extend from the apertures 204,212 in the direction of the outer edge 224 of the sheet 202 and are intended to break open to form a slot in the support 200 as will be described in greater detail below. The ends 226,228 of the lines of weakness 220,222 distal to their respective digit apertures 204,212 are configures so as to prevent the slots from reaching the outer edge 224 of the sheet 202. In the embodiment shown the support 200 is provided with four lines of weakness 220,222, with two lines 220 extending from the thumb aperture 204, and two lines 222 extending from the little finger aperture 212. It will be appreciated that a greater or lesser number of lines of weakness may be provided, and that the lines of weakness may extend from the edges of other digit apertures.

Figure 25:
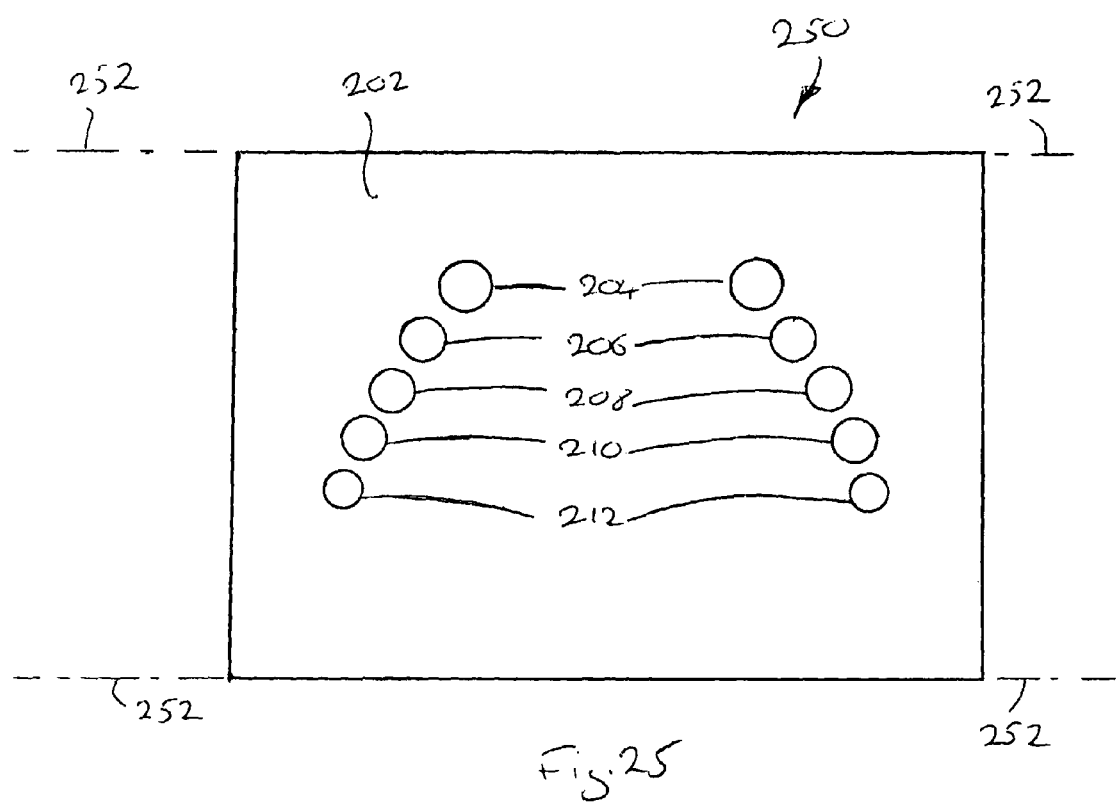
FIG. 25 shows a schematic view of a glove support configured to receive a pair of gloves.

Surrounding the digit apertures 204, 206, 208, 210, 212 there are provided a plurality of inner retaining slots 230, each of which extends through the sheet 202. In the embodiment shown, three retaining slots are spaced around both the thumb and little finger apertures 204,212, while the index, middle and ring finger apertures 206,208,210 are provided with two retaining slots 230 arranged on opposing sides thereof. It will be appreciated that other arrangements of retaining slots 230 may be provided. FIG. 25 illustrates a retaining slot 230 in greater detail. The slot 230 is dumbbell or barbell shaped and comprises substantially circular end portions 232 which are joined by a thinner, parallel sided centre section 234. The end portions 232 act to both prevent the slot from tearing or extending, and imbue a degree of flexibility to the flap like portions 236 of the sheet 202 provided either side of the centre section 234.

In an alternative embodiment the inner retaining slots 230 may be replaced by one or more retaining recesses or by one or more regions of adhesive which, in use, function in the same manner as the inner retaining slots 230.

Surrounding the retaining slots 230 there are provided four larger curved slots 238, 240 which, in use receive portions of the palm and cuff/sleeve of a glove fitted to the support 200. In an alternative embodiment the curved slots 238 may be replaced by one or more retaining recesses or by one or more regions of adhesive which, in use, function in the same manner as the curved retaining slots 238.

Surrounding the curved slots 238, 240 there is optionally provided a further ring of retaining slots 230. In an alternative, embodiment the further retaining slots 230 may be replaced by one or more retaining recesses or by one or more regions of adhesive which, in use, function in the same manner as the inner retaining slots 230.

The support 200 is further provided with a cuff retention lip 242. The lip 242 is provided in the opposite side of the support to that presented to a user when donning a glove. The lip 242 may be continuous or discontinuous depending upon the nature and configuration of the glove with which the support 200 is intended to be used. In an alternative embodiment the cuff retention lip 242 may be replaced by one or more retaining recesses, one or more retaining apertures or by one or more regions of adhesive which, in use, function in the same manner as the cuff retention lip 242.

FIG. 23 shows a cross-sectional view of the support 200 with a glove 300 mounted thereto. FIG. 23 also shows a breakable membrane 244 which maintains the fingers 302 of the glove in a folded arrangement in the vicinity of the digit apertures 204, 206, 208, 210, 212, as well as optional inner and outer peelable membranes 246,248 of the type described above in relation to earlier embodiments of the invention for maintaining the sterility of the glove 300 before use.

Figure 24:
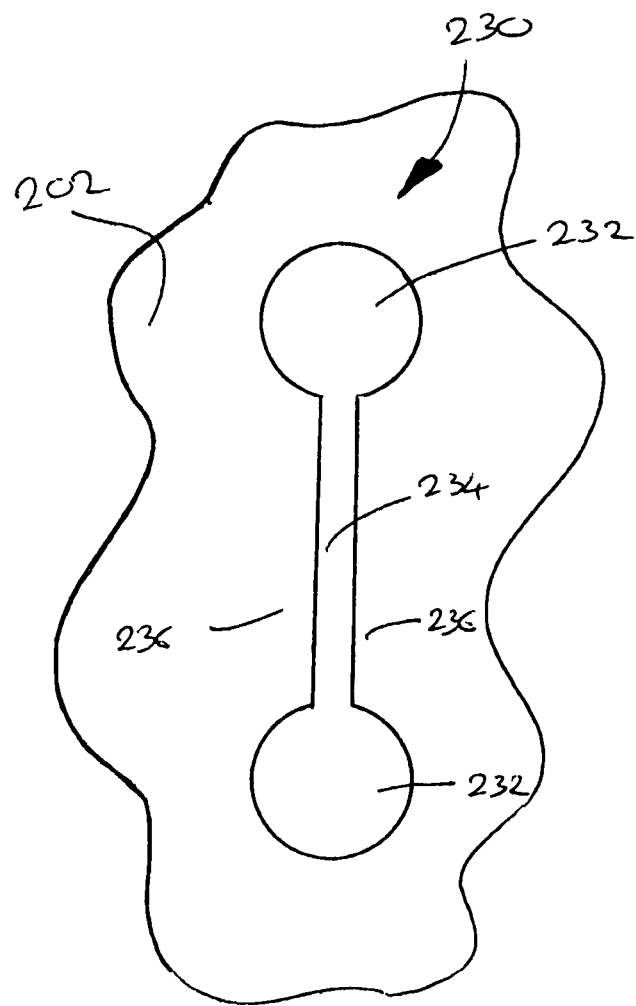
FIG. 24 shows a plan view of a glove retaining slot.

The glove 300 is mounted to the support 200 such that the fingers 302 of the glove 300 align with the digit apertures 204, 206, 208, 210, 212. Portions 304 of the glove 300 which surround the root of each glove finger 302 are received in the inner retention slots 230. The majority of the palm, back and cuff of the glove 300, generally designated 306 in FIG. 24 is received through the curved slots 238,240 and arranged in a rolled, folded, concertina or other like manner on the front side of the support 200. The cuff bead 308 is retained around the lip 242 while portions 310 of the glove 300 in the vicinity of the cuff bead 308 may be retained in the outer retaining slots 230 where provided. The inner retention slots hold the glove 300 such that openings to the fingers 302 of the glove 300 are positioned close to the digit apertures 204, 206, 208, 210, 212. The openings to the fingers 302 preferably lie close to or in the plane of the support 200.

In use, a user first removes the inner and/or outer membranes 246,248 if these are provided. This may be done manually by the user or automatically by a dispensing apparatus depending upon how the gloves are delivered to the user. The user then aligns the digits of their hand with the digit apertures 204, 206, 208, 210, 212 of the support 200. By moving their digits into the apertures 204, 206, 208, 210, 212 the user's fingers contact the fingers 302 of the glove 300. Continued movement of the users fingers through the apertures 204, 206, 208, 210, 212 leads to the breaking of the membrane 244 and the donning of the fingers 302 of the glove to the hand of the user. The movement of the hand of the user relative to the support 200 subsequently results in the disengagement of the glove portions retained by the inner retaining slots 230, the breaking of the webs 214 and the opening of the thumb and little finger weakness lines 220,222 to permit the palm and back portions of the hand of the user to pass through the support 200. The passage of the palm and back portions of the hand of the user through the support 200 draws the palm, back and cuff portions 306 of the glove 300 through the curved slots 238, 240 and on to the corresponding portions of the hand, wrist and forearm of the user dependent upon the configuration of the glove. The donning of the glove 300 is completed when the user has moved their hand through the support a sufficient distance to disengage the cuff bead 308 from the lip 242. The user can then withdraw their gloved hand from the support 200.

The glove 300 is retained with sufficient force by the inner retaining slots 302, lip 242 and optional outer retaining slots 230 to ensure that the glove is applied to the hand of the user without undue bagging or wrinkling. The intended partial destruction of the support 200 by the breaking of the webs 214 and the opening of the thumb and little finger weakness lines 220, 222 ensures that the support cannot be reused, and provides a visible indication to the user if an attempt has been made to reuse a support 200.

FIG. 25 shows a support 250 adapted for use with a pair of gloves. The arrangement of the digit apertures 204, 206, 208, 210, 212 is shown, however for the sake of clarity the weakness lines, retention slots and lip are omitted. The support 250 may form part of a strip, indicated by broken lines 252 which carries multiple pairs of gloves. Such a strip may be formed into a roll for subsequent use in an appropriately configured dispenser.

While the present invention is particularly suited to relatively thin and flexible gloves, such as for example latex procedure gloves, the present invention may be applied to other types of gloves.

The previously described embodiments relate to the provision of a single glove on a support. It will be appreciated that circumstances exist where by multiple gloving, i.e. the wearing of two or more gloves on a hand, is required. This can be achieved by donning two or more gloves sequentially or, alternatively, mounting two or more gloves nested one within the other to a support, so that the two or more gloves can be donned simultaneously.

The invention claimed is:

1. A support for a glove, the support being configured to releasably retain a glove in, a position which enables the glove to be donned by a user, the support comprising:
   (a) a planar body having at least one digit aperture shaped to receive the fingers of a user;
   (b) an inner glove retaining arrangement comprising apertures extending through the body into which portions of a glove may be placed provided around the at least one digit aperture; and
   (c) an outer glove retaining arrangement comprising a projection of the body configured to receive the cuff bead of a glove provided around both the inner glove retaining arrangement and the at least one digit aperture,
   wherein the body includes at least one weakened region extending from the at least one digit aperture, the weakened region, in use, permitting the body to separate and thereby increase the size of the at least one digit aperture as the hand of a user is inserted into the at least one digit aperture.

2. A support as claimed in claim 1 wherein the at least one weakened region is defined by a line of perforations in the body.

3. A support as claimed in claim 1 wherein the body is provided with a plurality of digit apertures shaped to receive the fingers of a user.

4. A support as claimed in claim 1 wherein the support is provided with a glove storage arrangement which is provided between the inner and outer glove retaining arrangements.

5. A support as claimed in claim 4 wherein the glove storage arrangement comprises one or more apertures of the body through which portions of a glove may pass, in use.

6. A support as claimed in claim 4 wherein the support is provided with an additional glove retaining arrangement which is positioned between the glove storage arrangement and the outer glove retaining arrangement.

7. A support as claimed in claim 6 wherein the additional glove retaining arrangement comprise a plurality of apertures of the body which surround the glove storage arrangement of the support.

8. A support as claimed in claim 1 and configured to releasably retain a plurality of gloves.

9. A support as claimed in claim 1 and configured to releasably retain a plurality of pairs of gloves.

10. A support as claimed in claim 8 wherein the planar body of the support is elongate and flexible so as be formable into a roll.

11. In combination, a support as claimed in claim 1 and a glove, wherein the cuff of the glove is releasably retained by the outer glove retaining arrangement and portions of the palm and back of the glove which surround the base of the fingers of the glove are retained in the inner glove retaining arrangement such that the fingers of the glove are aligned with the at least one digit aperture.

12. The combination of a support and a glove as claimed in claim 11 wherein the support is provided with a protective cover to form a sealed compartment with the support, and wherein the external surface of the glove is positioned on the interior of the sealed compartment.

13. The combination as claimed in claim 12 wherein the cover is adapted to detach for the support when the glove is donned by a user.

14. The combination as claimed in claim 12 wherein the cover is adapted to break when the glove is donned by a user.

15. The combination as claimed in claim 12 wherein the compartment is sterile.

16. The combination as claimed in claim 12 wherein the cover fits closely to the support and holds the fingers of the glove close to the support in the region of the at least one digit aperture.

17. The combination of a support and a glove as claimed in claim 16 wherein the fingers of the glove are folded, rolled, held in a concertina fashion or otherwise stored in the compartment defined between the support and the cover.

18. The combination of a support and a glove as claimed in claim 11 wherein the support is provided with an additional cover on the side of the support which faces the user, in use, the additional cover overlying the at least one digit aperture.

19. The combination as claimed in claim 11 wherein the support is provided with a further cover which overlies the protective cover and which is removable prior to the user donning the glove.

20. The combination as claimed in claim 11 wherein a plurality of gloves are releasably retained by the support.

21. The combination as claimed in claim 11 wherein a plurality of pairs of gloves are releasably retained by the support.

22. The combination as claimed in claim 20 wherein the planar body of the support is elongate and flexible so as be formable into a roll.

23. A method of donning a glove onto a hand of a user using a glove support, the method comprising the steps of:
   (a) providing a support comprising
      (i) a planar body having at least one digit aperture shaped to receive the fingers of a user, (ii) an inner glove retaining arrangement comprising apertures extending through the body into which portions of a glove may be placed provided around the at least one aperture, and (iii) an outer glove retaining arrangement comprising a projection of the body configured to receive the cuff bead of a glove provided around both the inner glove retaining arrangement and the at least one aperture, wherein the body includes at least one weakened region extending from the at least one digit aperture;

(b) providing a glove mounted to the support such that the cuff of the glove is releasably retained by the outer glove retaining arrangement and portions of the palm and back of the glove which surround the base of the fingers and thumb of the glove are retained in the inner glove retaining arrangement such that the finger and thumb of the glove are aligned with the at least one digit aperture;

(c) aligning the fingers and thumb of the hand of the user with the finger and thumb portions of the glove;

(d) inserting the fingers and thumb of the hand into the finger and thumb portions of the glove through the at least one digit aperture;

(e) moving the hand of the user through the at least one digit aperture to cause the weakened region of the support to break and thereby enlarge the at least one digit aperture, the continued movement of the hand of the user causing the glove to become disengaged from the inner and then the outer glove retaining arrangements and become donned to the hand of the user; and (e) retrieving the gloved hand by moving it back through the enlarged aperture.

* * * * *